(12) United States Patent
Baruch et al.

(10) Patent No.: US 9,909,102 B2
(45) Date of Patent: Mar. 6, 2018

(54) FLUIDIC DEVICE FOR PRODUCING PLATELETS

(71) Applicants: PLATOD, Paris (FR); ECOLE SUPÉRIEURE DE PHYSIQUE ET DE CHIMIE INDUSTRIELLES DE LA VILLE DE PARIS, Paris (FR)

(72) Inventors: Dominique Baruch, Paris (FR); Antoine Pierre Marin Blin, Paris (FR); Aurelie Magniez, Villejuif (FR); Sonia Chassac, Ju-visy-sur-Orge (FR); Anne Le Goff, Paris (FR); Mathilde Reyssat, Antony (FR)

(73) Assignees: PLATOD, Paris (FR); ECOLE SUPÉRIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 106 days.

(21) Appl. No.: 15/037,191

(22) PCT Filed: Nov. 18, 2014

(86) PCT No.: PCT/EP2014/074905
§ 371 (c)(1),
(2) Date: May 17, 2016

(87) PCT Pub. No.: WO2015/075030
PCT Pub. Date: May 28, 2015

(65) Prior Publication Data
US 2016/0272941 A1 Sep. 22, 2016

(30) Foreign Application Priority Data
Nov. 19, 2013 (EP) .................................. 13306582

(51) Int. Cl.
*C12M 3/00* (2006.01)
*C12N 5/078* (2010.01)
(Continued)

(52) U.S. Cl.
CPC ...... *C12N 5/0644* (2013.01); *B01L 3/502715* (2013.01); *B01L 3/502753* (2013.01);
(Continued)

(58) Field of Classification Search
CPC ...................................................... C12M 3/00
See application file for complete search history.

(56) References Cited

FOREIGN PATENT DOCUMENTS

| JP | 2013031428 A | 2/2013 |
| WO | 2010063823 A1 | 6/2010 |

(Continued)

OTHER PUBLICATIONS

Chang et al., "Biomimetic technique for adhesion-based collection and separation of cells in a microfluidic channel," 2005, 64-73, vol. 5, The Royal Society of Chemistry.
(Continued)

*Primary Examiner* — Rosanne Kosson
(74) *Attorney, Agent, or Firm* — Whitham, Curtis & Cook, P.C.

(57) ABSTRACT

The invention relates to a fluidic device for producing platelets from a suspension of megakaryocytes or their fragments, comprising a production chamber comprising at least one channel in which a suspension of megakaryocytes is introduced to flow from its inlet to its outlet wherein said channel is textured with a plurality of obstacles on at least one portion of its inner surface. The invention is further directed to an ex vivo method for producing platelets from megakaryocytes using a fluidic device as defined above.

27 Claims, 14 Drawing Sheets

(51) Int. Cl.
*B01L 3/00* (2006.01)
*G01N 15/10* (2006.01)
*A61K 35/12* (2015.01)
*G01N 15/00* (2006.01)

(52) U.S. Cl.
CPC .... *B01L 3/502761* (2013.01); *G01N 15/1056* (2013.01); *A61K 2035/124* (2013.01); *B01L 2200/0647* (2013.01); *B01L 2200/0663* (2013.01); *B01L 2300/0809* (2013.01); *B01L 2300/0848* (2013.01); *B01L 2300/0861* (2013.01); *B01L 2300/16* (2013.01); *B01L 2400/086* (2013.01); *C12N 2501/125* (2013.01); *C12N 2501/145* (2013.01); *C12N 2521/00* (2013.01); *C12N 2533/50* (2013.01); *G01N 2015/0084* (2013.01); *G01N 2015/1081* (2013.01)

(56) References Cited

FOREIGN PATENT DOCUMENTS

| WO | 2010102335 A1 | 9/2010 |
|---|---|---|
| WO | 2012129109 A2 | 9/2012 |
| WO | 2013030155 A1 | 3/2013 |
| WO | 2014107240 A1 | 7/2014 |

OTHER PUBLICATIONS

Dunois-Larde et al., "Exposure of human megakaryocytes to high shear rates accelerates platelet production," Jan. 18, 2010, 1875-1883, vol. 114, No. 9, The American Society of Hematology.

Nakagawa et al., "Two differential flows in a bioreactor promoted platelet generation from human pluripotent stem cell-derived megakaryocytes," Apr. 12, 2013, 742-748, Society for Hematology and Stem Cells.

Pallotta et al., "Three-Dimensional System for the In Vitro Study of Megakaryocytes and Functional Platelet Production Using Silk-Based Vascular Tubes," 2011, 1223-1233, vol. 17, No. 12, Tissue Engineering: Part C.

Stott et al., "Isolation of circulating tumor cells using a microvortex-generating herringbone-chip," Oct. 26, 2010, 18392-18397, vol. 107, No. 43, PNAS.

Sullenbarger et al., "Prolonged continuous in vitro human platelet production using three-dimensional scaffolds," 2009, 101-110, vol. 37, Experimental Hematology.

Thon et al., "Platelet bioreactor-on-a-chip," Jul. 21, 2014, 2 pages.

FLUIDIC DEVICE FOR PRODUCING PLATELETS

RELATED PATENT APPLICATIONS

The present patent application is filed pursuant to 35 U.S.C § 371 as a U.S. National Phase application of International Patent Application No. PCT/EP2014/074905, which was filed on Nov. 18, 2014, claiming the benefit of priority to European Patent Application No. 13306582.1 filed on Nov. 19, 2011. The content of each of the aforementioned patent applications the European patent application is incorporated herein by reference in its entirety.

FIELD OF THE INVENTION

The present invention relates to an improved method for producing platelets from megakaryocytes or their fragments.

BACKGROUND OF THE INVENTION

Blood platelets are small anucleate cells that are crucial for the arrest of bleeding. There are many clinical diseases where platelet production or function is impaired and the number of patients who require platelet transfusion is increasing. Presently, the solution consists in conducting transfusions of platelets obtained from blood donors. Ex vivo platelet production for therapeutic applications is an appealing alternative, but remains a major technological challenge.

Platelets originate from megakaryocytes. Megakaryocyte differentiation is a continuous process characterized by sequential steps. While megakaryocyte differentiation takes place in the bone marrow, platelet production requires the passage of megakaryocyte fragments into the vessels of the bone marrow. Attempts of designing bioreactors specifically dedicated to platelet production have been made.

The international patent application WO 2010/06382311 discloses an ex vivo method for producing platelets from mature megakaryocytes by subjecting a suspension of mature megakaryocytes to a flow having a shear rate of at least 600 $s^{-1}$ on a solid phase coated with von Willebrand factor (VWF). The shear rate influence is further discussed in the scientific article of Dunois-Lardé et al. ("Exposure of human megakaryocytes to high shear rates accelerates platelet production", Blood, vol. 114, no 9, p. 1875-1883, 2009). However, the production yield still needs to be improved for potential therapeutic applications.

Some publications suggest the use of 3D systems designed to reproduce the natural bone marrow environment (see Pallotta et al, "Three-Dimensional System for the In Vitro Study of Megakaryocytes and Functional Platelet Production Using Silk-Based Vascular Tubes", Tissue Engineering: Part C, vol. 17, no 12, p. 1223-1232, 2011, and Sullenbarger et al., "Prolonged continuous in vitro human platelet production using three-dimensional scaffolds", Experimental Hematology, vol. 37, no 1, p. 101-110, 2009). In these systems, cells fragments freely migrate from a scaffold in which cells are embedded into a flowing channel through porosity or tubes. In addition, Nakagawa et al ("Two differential flows in a bioreactor promoted platelet generation from human pluripotent stem cell-derived megakaryocytes", Experimental Hematology, 2013 vol. 41, no 8 p 742-748, 2013) recently disclose two new bioreactors which mimic a capillary blood vessel for platelet production. They comprise a porous structure or slits able to trap megakaryocytes. A pressure flow is applied to ensure the fixation of the megakaryocytes. In addition, a main flow is applied perpendicular to the pressure flow or with an angle of 60° between pressure flow and main flow. Said main flow applies shear stress to the trapped megakaryocytes. However, the main flow remains free of megakaryocytes. Megakaryocyte fragments are subjected to the main flow and released platelets are collected at the outlet of the main flow. Thon et al («Platelet bioreactor-on-a-chip», Blood, vol 124, no 12 p 1857-1867, 2014) describe another bioreactor based on a feeding channel and main channel flow parallel to one another, separated by a wall pierced with slits. When the end of the feeding channel is closed, megakaryocytes are pushed through the slits. There, they are brought into contact with the main flow and experience shear stress. In such systems, the number of sites available for megakaryocytes is limited, and many cells stay stuck in the reservoir while the first ones elongate and release platelets. This limits the speed of the platelet production process. These system geometries are not efficient for rapid large-scale production. In addition, the obtained production yields are still not sufficient, a fact that renders difficult the functional characterization of platelets. Furthermore, experiments performed over several hours or days have an intrinsic platelet shedding that is seldom evaluated.

Microfluidic devices with specific structure have been disclosed for different biological applications. For instance, Stott et al. ("Isolation of circulating tumor cells using a microvortex-generating herringbone-chip", PNAS, vol. 107, no 43, p. 18392-18397, 2010) describe the use of a microfluidic device whose inner surface is coated with antibodies for isolation of circulating tumor cells. Grooves were formed in the inner surface, so as to disrupt the laminar flow streamlines inside the channel, and to increase the number of cell-surface interactions in the antibody-coated device. Similarly, Chang et al. ("Biomimetic technique for adhesion-based collection and separation of cells in a microfluidic channel", Lab Chip, vol. 5, p. 64-73, 2005) teach the use of a microfluidic channel containing arrays of micropillars to separate and collect cells. However, contrary to the present invention, the object of such microfluidic device is not to trigger platelet shedding from megakaryocytes.

One object of the present invention is therefore to provide a fluidic device for producing platelets from a suspension of cells comprising megakaryocytes or their fragments, in particular suitable for high yield production while maintaining the functional qualities of the newly generated platelets. Another object of the invention is to provide a method for producing platelets suitable to large-scale production of high quality and standardized platelets.

SUMMARY OF THE INVENTION

In one aspect, the invention relates to a fluidic device (1) for producing platelets from a suspension of megakaryocytes (5), comprising:
- a production chamber (3) comprising at least one channel (8) in which a suspension of cells comprising megakaryocytes or their fragments can be introduced to flow from its inlet (9) to its outlet (10);
- optionally a flow rate controller (7) for controlling the flow of said suspension in the channel (8);
- optionally a megakaryocyte sorter and/or a mixer (2) for enriching the suspension with megakaryocytes and homogenizing cell concentration of said suspension of megakaryocytes, upstream of the production chamber (3);

optionally a platelet sorter (4) downstream from the production chamber (3) for purifying the outflow suspension (6) by sorting platelets from megakaryocytes or other cell residues;

wherein at least one portion (11) of the inner surface of the walls of said channel (8) is textured with a plurality of obstacles.

In a related aspect, the invention relates to fluidic device for producing platelets from a suspension of cells comprising megakaryocytes or their fragments, comprising:

a production chamber (3) comprising at least one channel (8) delimited by non-porous walls, and at least one inlet opening (9) at one end of the channel, in which a suspension of cells comprising megakaryocytes or their fragments can be introduced, and at least one outlet opening (10) at the other end of the channel, in which platelets can be collected;

optionally a flow rate controller (7) for controlling the flow of said suspension in the channel (8);

optionally a megakaryocyte sorter and/or a mixer (2) for enriching the suspension with megakaryocytes and homogenizing cell concentration of said suspension of megakaryocytes, upstream of the production chamber (3);

optionally a platelet sorter (4) downstream from the production chamber (3) for purifying the outflow suspension (6) by sorting platelets from megakaryocytes or other cell residues;

wherein at least one portion (11) of the inner surface of the walls of said channel (8) is textured with a plurality of obstacles.

In specific embodiments, said plurality of obstacles are distributed over a two-dimensional surface, thereby forming a three-dimensional array of obstacles.

In another aspect, the invention is directed to an ex vivo method for producing platelets from megakaryocytes or their fragments, said method comprising:

introducing a suspension of cells comprising megakaryocytes or their fragments into a fluidic device as defined above;

subjecting said suspension to a flow under shear rate suitable for elongation, fragmentation of the megakaryocytes and platelet release in the channel of the production chamber; and collecting platelets at the outlet of the channel.

DETAILED DESCRIPTION OF THE INVENTION

This invention will now be described in further details. In the following description, the expression "comprised between" should be understood to designate the range of values identified, including the lower and upper bounds.

The invention is directed to a fluidic device for producing platelets from a suspension of megakaryocytes, or their fragments.

As used herein, the term "platelets" denotes the anucleate cells that are involved in the cellular mechanisms of primary hemostasis leading to the formation of blood clots.

As used herein, the term "proplatelets" denotes any structural form of a megakaryocyte or its fragments, such as cytoplasmically-linked platelet-like particles, that could result in platelet formation. The structural forms include, but are not limited to, cells with long cytoplasmic extensions, projections or pseudopodia that contain swellings encompassing platelet bodies in various stages of formation, such as, nodules, beads, and the like.

As used herein, the term "megakaryocyte" denotes a bone marrow cell responsible for the production of blood platelets necessary for normal hemostasis. Megakaryocytes are derived from hematopoietic progenitors restricted to the megakaryocytic lineage. The primary signal for megakaryocyte production is thrombopoietin or TPO. TPO is necessary for inducing differentiation of progenitor cells in the bone marrow towards a final megakaryocyte phenotype. Other molecular signals for megakaryocyte differentiation include for example GM-CSF, IL-3, IL-6, IL-11, Flt-3 ligand and SCF. Megakaryocyte progenitor cells can be obtained by in vitro culture.

Typically, the suspension of megakaryocytes comprises a population of megakaryocytes suspended in an appropriate cell culture medium. In one embodiment, said cell culture medium is Iscove's Modified Dulbecco's Medium (IMDM), supplemented with BIT serum substitute, α-monothioglycerol and liposomes. The suspension may further comprise fragments of megakaryocytes or proplatelets.

In one specific embodiment, the suspension of mature megakaryocytes is preferably obtained by the following steps:
(i) providing megakaryocyte progenitor cells
(ii) culture expanding said megakaryocyte progenitor cells,
(iii) differentiating the expanded cells into megakaryocytes The megakaryocyte progenitor cells are for example selected from hematopoietic stem cells (for example, from umbilical cord, peripheral blood or bone marrow), or from stem cells selected from the group consisting of embryonic stem cells and induced pluripotent stem cells.

In some embodiments, though a majority of the cells of the suspension may be megakaryocytes, other cells or cell residues may be found in minor amounts in such suspension, including without limitation, megakaryocyte progenitor cells, cytoplasmic fragments and proplatelets. In one embodiment, the suspension of cells comprising megakaryocytes for use in the devices or methods according to the invention thus further comprise fragments of megakaryocytes, and in particular proplatelets or platelets. For example, a majority of cells comprising megakaryocytes, may express CD41 and CD42b antigens on their membrane, Details for the production of megakaryocyte from progenitors or stem cells may be found for example in "Balduini A, Pallotta I, Malara A, Lova P, Pecci A, Viarengo G, Balduini C L, Torti M. Adhesive receptors, extracellular proteins and myosin HA orchestrate proplatelet formation by human megakaryocytes. *J Thromb Haemost*. 2008; 6: 1900-7." or in "Takayama N, Nishimura S, Nakamura S, Shimizu T, Ohnishi R, Endo H, Yamaguchi T, Otsu M, Nishimura K, Nakanishi M, Sawaguchi A, Nagai R, Takahashi K, Yamanaka S, Nakauchi H, Eto K. Transient activation of c-MYC expression is critical for efficient platelet generation from human induced pluripotent stem cells. *The Journal of Experimental Medicine*. 2010; 207: 2817-30.".

In one embodiment, the suspension of megakaryocytes introduced to flow in the device presents a cell concentration comprised between $10^3$ and $10^8$ per mL, preferably between $10^5$ and $5 \cdot 10^6$ per mL.

The fluidic device according to the invention comprises at least one production chamber comprising at least one channel having at least two openings, which may be further described as the inlet and the outlet of the channel. The channel is such that a suspension of megakaryocytes or their fragments may flow from its inlet to its outlet. Preferably, the channel has one inlet and one outlet and a main flow can be applied for the suspension of megakaryocytes to flow from said inlet to said outlet.

In specific embodiments, the production chamber may be further divided into several parallel channels, each of them delimited by non-porous walls, with at least one inlet opening (9) at one end of the chamber in which a suspension of cells comprising megakaryocytes can be introduced and at least one outlet opening (10) at the other end in which platelets can be collected, said channel forming a single flow from its inlet to its outlet.

As used herein, the term "non-porous" means that the megakaryocytes or their fragments (including platelets or proplatelets) cannot cross the walls and thereby remain in the main flow from the inlet to the outlet of the channel.

The inventors have discovered that, in order to produce platelets with a high yield, the channel of the fluidic device has to be textured on at least one portion of its inner surface, i.e. on at least one portion of the surface of the channel's wall which is intended to be in contact with the suspension of megakaryocytes. The texture is generated by a plurality of obstacles. Preferably, said obstacles are distributed on at least one 2-dimensional surface of the channel, thereby forming a 3-dimensional array of obstacles. Because of said obstacles, the inner surface of the channel is not smooth. The inventors discovered that, when flowing through a textured channel, the capture of megakaryocytes on the textured surface and their shedding into platelets are improved. Typically, at least one portion of the inner surface of said channel is textured with at least one three dimensional array of obstacles distributed on at least one surface of the channel to modify the distance between neighboring streamlines allowing the capture of flowing megakaryocytes on the surfaces of obstacles and/or on the inner surface of the channel and expose them to shear so as to induce platelet shedding. The platelets that are generated by exposure of megakaryocytes to the flow through the textured channel, display some functional aspects resembling those of the circulating blood platelets. Platelets generated in the microfluidic device may be different from platelet-like particles. These platelet-like particles may be formed without passing through the microfluidic chips and are not entirely functional. In particular, in specific embodiments, the platelets produced in the device of the present invention can be activated, like natural platelets or circulating blood platelets, in contrast to platelet-like particles, which cannot be activated.

According to a preferred embodiment of the invention, the textured portion of the inner surface of the channel may be further coated with a ligand with binding affinity for megakaryocytes, e.g., von Willebrand factor (VWF) or its functional variants. Such ligand may have specific affinity for platelets and/or megakaryocytes or their specific receptors, or, non-specific affinity for platelets and/or megakaryocytes. Such coating increases cell adhesion to the inner wall or obstacles of the channel.

As used herein, the term "von Willebrand factor" or "VWF" denotes the multimeric protein consisting of several monomers involved in hemostasis. An exemplary amino acid sequence of human von Willebrand factor can be found in the GenPept database under accession number AAB59458. Preferably the von Willebrand factor according to the invention is a mammalian Von Willebrand factor, even more preferably a murine factor or a primate factor, even more preferably human von Willebrand factor. The term "VWF" encompasses VWF of any mammalian origin, such as primate VWF, preferably human VWF. According to the invention, the VWF factor can be recombinant VWF or native VWF. In its native form, it can be purified or can be comprised in a composition comprising other components (e.g. in an extracellular matrix). The skilled person can also easily produce such recombinant VWF according to standard techniques in the art, for example using transfected host cells capable of producing said recombinant VWF or its functional variants.

As used herein, the term "functional variant" of VWF, refers to natural or recombinant fragment of VWF factor, or homologue or analogue of VWF retaining the capacity to bind to GPIb, especially human GPIb.

A homologue of VWF is a polypeptide with an amino acid sequence which shares at least 50% identity, preferably, at least 60%, 70%, 80%, 90%, and 95% identity to human VWF amino acid sequence.

As used herein, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Myers and W. Miller (Comput. Appl. Biosci. 4: 1 1-17, 1988) which has been incorporated into the ALIGN program. In addition, the percent identity between two amino acid sequences can be determined using the Needleman and Wunsch (J. Mol. Biol. 48:443-453, 1970) algorithm which has been incorporated into the GAP program in the GCG software package. Yet another program to determine percent identity is CLUSTAL (M. Larkin et al., Bioinformatics 23:2947-2948, 2007; first described by D. Higgins and P. Sharp, Gene 73:237-244, 1988) which is available as stand-alone program or via web servers (see http://www.clustal.org).

Variants further include polypeptide or fusion protein comprising a fragment of VWF factor fused to a heterologous polypeptide sequence which is not naturally linked to said VWF. Other variants include multimeric forms of VWF domains, wherein said VWF domains are those fragments of VWF which have affinity to GPIb.

As used herein, the term "fragments" include natural or recombinant partial amino acid sequence of at least 5, preferably at least 10 or at least 20 consecutive amino acids of a given polypeptide.

Examples of variants of VWF which can be used for coating the device of the present invention include, without limitation, recombinant VWF-A1 (amino acids Q1238-P1471) polypeptides, which can be expressed in *Escherichia coli*, or recombinant VWF-A1A2A3 (amino acids D1261-G1874) polypeptide, which can be expressed in mammalian cells and purified as previously described in Martin, C., Morales, L. D. and Cruz, M. A. (2007), Journal of Thrombosis and Haemostasis, 5: 1363-1370. doi: 10.1111/j.1538-7836.2007.02536.x.

Alternatively the skilled person may select analogues of VWF, i.e. a protein or polypeptide which does not share sequence homology with VWF primary amino acid sequence, but exhibit similar properties of megakaryocyte and/or platelet binding affinity. Such analogues may be selected without limitation from the group consisting of fibrinogen, fibronectin, laminin, collagen and tenascin.

The channel of the fluidic device according to the invention may be defined by its length L between its inlet and its outlet. The cross-section of the channel, which may be preferably the same on the whole length of the channel, may be round, ovoid, rectangular or square. As used herein, the height H of the channel refers to the smallest distance measured between two opposite walls in a section of the channel. For example, in a circular section, the height H of the channel is the diameter of the circular section of the channel. According to one preferred embodiment, said channel may have a substantially square or rectangular section, with bottom and upper walls determining the channel height H, and side walls determining the channel width W. The channel is preferably straight and the axis of the straight channel defines the longitudinal direction of the channel.

According to a preferred embodiment of the invention, the fluidic device is a microfluidic device, i.e. one of the dimensions of the cross-section of the device is smaller than 1 millimeter. The channel may be called microchannel.

With regards to the dimension of the channel, these may be optimized depending on the average size of the megakaryocytes that could be used for platelet production. Such parameter called $D_{cell}$ throughout the specification is defined as the mean megakaryocyte diameter in the suspension for use in the method of the present invention, and can be measured by different techniques, as impedance cell counter detection (for example a Coulter counter as described in U.S. Pat. No. 2,656,508) or optical microscopy followed by image analysis.

Depending on the source of precursor cells and the megakaryocyte production method that are used, $D_{cell}$ may typically be comprised between 5 μm and 150 μm, for example between 7 μm and 100 μm, and for example between 10 and 50 μm. In specific embodiments, the dimensions of the device of the invention are optimized for $D_{cell}$ being selected among the following sizes: 15 μm, 20 μm, 25 μm, 30 μm, 35 μm, 40 μm and 45 μm.

In specific embodiments, the height H of the channel may be comprised between $D_{cell}$ and 1 mm, preferably between $D_{cell}$ and 100 μm. The width W of the channel may be comprised between $D_{cell}$ and 1 m, preferably between $10 \times D_{cell}$ and 1 cm. The length L of the channel may be comprised between 1 mm and 10 m, preferably between 10 mm and 1 m, and more preferably between 10 cm and 1 m.

The production chamber of the fluidic channel of the invention may comprise one single channel or a plurality of channels, which may be different or identical. When a plurality of channels is used, parallelized channels share the same flow inlet (16) and flow outlet (17). According to a preferred embodiment of the invention, the production chamber may comprise a plurality of parallelized channels. The number N of channels in the production chamber may be comprised between 2 and 1,000,000, preferably between 2 and 100,000.

When parallelized channels are used, the production chamber preferably further comprises a distribution channel, which distributes the inlet suspension to every channel. The distribution channel may have a triangular shape. Advantageously, the shape of the distribution channel is such that it avoids damaging the cells with a too high shear rate, for instance by having a higher height than the one used in the parallelized channels.

The inner surface of the channel is textured on at least one portion. Said textured portion of the channel may have a length comprised between 1% of the length L of the channel and 100% of the length of the length L of the channel, preferably, between 50% of the length L of the channel and 100% of the length L of the channel.

The texture is generated by a plurality of obstacles. The density, size and shape of said obstacles may be determined so as to capture megakaryocytes on the surface of obstacles and/or of the inner channel walls for further platelet shedding.

As used herein, the term "capture" means that the megakaryocytes contact the surface of obstacles and/or the inner channel and are strongly slowed down, as compared to the mean velocity of the flow. The megakaryocytes can be possibly stopped after contacting the surface of an obstacle.

The obstacles may have for instance the shape of posts, pillars, beams, crescent, pierced-crescent, stars, cavities or pyramids. Preferably, the obstacles are posts or beams. A post may preferably have a square or round or triangle cross-section, and it can be defined by its radius r and its height h. As used therein, the "radius" of the post is defined as the half of the largest dimension of the cross-section of the post. A beam may preferably have a rectangular or square cross-section, and it can be defined by its length $l_{beam}=W$, by its width $w_{beam}=2r$ and its height h.

With regards to the dimension of the posts: the height h of the posts may preferably be comprised between 0 and H, and more preferably between $D_{cell}/2$ and $(H-D_{cell}/2)$. The radius r of the posts may preferably be comprised between $D_{cell}/100$ and $100 \times D_{cell}$, more preferably between $D_{cell}/10$ and $10 \times D_{cell}$. $D_{cell}$ being often comprised between 5 and 150 μm, the height h of the posts may preferably be comprised between 0 and 1 mm. The radius r of the posts may preferably be comprised between 50 nm and 15 mm, more preferably between 500 nm and 1.5 mm.

With regards to the dimension of the beams: the height h of the beams may preferably be comprised between 0 and H, and more preferably between $D_{cell}/2$ and $(H-D_{cell}/2)$. The width 2r of the beams may preferably be comprised between $D_{cell}/10$ and $100 \times D_{cell}$, and more preferably between $D_{cell}$ and $10 \times D_{cell}$. $D_{cell}$ being often comprised between 5 and 150 μm, the height h of the beams may preferably be comprised between 0 and 1 mm.

The width 2r of the beams may preferably be comprised between 500 nm and 15 mm, more preferably between 5 μm and 1.5 mm.

The obstacles may be placed on the inner surface of the channel randomly or according to a specific pattern. Consequently, the texture may be irregular or regular. A regular pattern may be characterized by some features like its periodic structure, the lattice pitch and the tilt of the lattice direction with regard to the longitudinal direction of the channel. If the pattern is irregular, it may be characterized by the density of the obstacles or by the mean distance between obstacles.

According to a preferred embodiment of the invention, the obstacles may be arranged on the inner surface of at least one portion of the channel to form a regular pattern.

According to another embodiment, the obstacle density may vary along the channel.

According to one specific embodiment, the obstacles are posts with a substantially circular section of a radius r, and said posts are arranged on the inner surface of at least one portion of said channel to form a regular pattern with a hexagonal periodic structure such as:
  (i) the closest distance p between two post centers is at least equal to 2r, preferably between $(2r+D_{cell}/10)$ and $(2r+100 \times D_{cell})$, even better between $(2r+D_{cell})$ and $(2r+10 \times D_{cell})$;
  (ii) the angle α, which is the lowest angle defined by the longitudinal direction of the channel and one of the lattice vectors of the primitive cell of the hexagonal periodic structure, is such as:
when r≥$D_{cell}$/2, α is comprised between $$\arcsin\left(\frac{r}{10p}\right) \text{ and } \arcsin\left(\frac{2r}{p}\right),$$

when r<$D_{cell}$/2, α is comprised between $$\arcsin\left(\frac{D_{cell}}{20p}\right) \text{ and } \arcsin\left(\frac{D_{cell}}{p}\right),$$

(iii) optionally said posts have a height h such as 0<h≤H, preferably $D_{cell}$/2<h≤(H−$D_{cell}$/2), wherein H is the height of the channel.

In one specific embodiment, the obstacles are posts (12) with a substantially circular section of a radius r, and said posts are arranged on the inner surface (13) of at least one portion of said channel to form a regular pattern with a hexagonal periodic structure such as:
  (i) the radius of a post r is preferably between 50 nm and 15 mm, more preferably between 500 nm and 1.5 mm;
  (ii) the closest distance p between two post centers is at least equal to 100 nm, preferably between 100 nm and 50 mm, preferably between 500 nm and 10 mm, even better between 5 µm and 1 mm;
  (iii) the angle α, which is the smallest angle defined by the longitudinal direction of the channel (14) and one of the lattice vectors of the hexagonal Bravais lattice is such as a is comprised between 0 and 90° and preferably between 0 and 30°;
  (iv) optionally said posts have a height h such as 0<h≤H, wherein H refers to the smallest distance measured between two opposite walls in a section of the channel.

The fluidic device may preferably be made according to commonly known techniques of fabrication of microfluidic system, for instance by soft lithography (Xia et al. 1998. "Soft lithography". *Annual Review of Materials Science*. vol. 28, no 1, p. 153-184).

A master of the device with positive relief of the at least partly textured channel may be prepared by conventional methods: one method may consist in producing transparencies from a computer assisted design file containing the design of the channel. After that, these transparencies may be used as masks in transferring the pattern into a negative photoresist to form the master.

The fluidic device may be made of polydimethylsiloxane (PDMS) and sealed on glass slides. This material is advantageous for having a visual control of the device. However, other materials like silicon, glass, polystyrene, polycarbonate, polyvinyl chloride, cyclic olefin copolymer, poly(m-ethyl methacrylate), thermoset polyester, polyurethane methacrylate, Norland Optical Adhesive, hydrogels (e.g. alginate, collagen, agarose, polyacrylamide, polysaccharide) can be used for the fabrication of the fluidic device.

Advantageously, the fluidic device and more specifically the production chamber allows to work under sterile conditions. In a preferred embodiment, said fluidic device is sterile. The method for producing the fluidic device according to the invention may comprise the step of sterilization of the device. This sterilization step may occur before or after the sealing of the device.

In addition, the production method may comprise the step of coating at least the textured portion of the inner surface of the channel with a ligand with binding affinity for megakaryocytes, e.g., von Willebrand factor (VWF) or its functional variants. In a particular embodiment, the inner surface of the channel is coated by incubation with a solution of von Willebrand factor or its functional variants. Typically the concentration of VWF used for coating the solid phase is between 5 and 100 µg/mL. In a preferred embodiment, the concentration of VWF is between 20 and 40 µg/mL. In one embodiment, the inner surface of the channel is coated with functional variants of VWF selected from the group consisting of recombinant wild-type VWF or mutated VWF polypeptides, expressed in *E. Coli* or in mammalian cells, as monomeric or dimeric polypeptides.

In addition to a production chamber, the fluidic device according to the invention may comprise optional means such as:
  a flow rate controller for controlling the flow of said suspension in the channel;
  optionally a megakaryocyte sorter and/or a mixer for enriching the suspension with megakaryocytes and homogenizing cell concentration of said suspension of megakaryocytes, upstream of the production chamber.
  optionally a platelet sorter downstream from the production chamber for purifying the outflow suspension by sorting platelets from megakaryocytes or other cell residues;

The flow rate controller may be placed on the channel so as to control the flow rate preferably at the inlet of the channel or at the outlet of the channel. This means may optionally be coupled with a pump, which generates the flow of the suspension of megakaryocytes into a fluidic device.

The use of a megakaryocyte sorter upstream of the production chamber may be advantageous to obtain a suspension homogeneous in terms of cell population and to obtain consistent yield and quality for industrial production of platelets. In particular, the megakaryocyte sorter includes means to separate the megakaryocytes from platelets and other cell residues. Conventional cell sorter as described below for the platelet cell sorter may be used. In particular, the use of a megakaryocyte sorter allows to obtain a cell suspension enriched in megakaryocytes, i.e. wherein at least 50%, preferably at least 70%, 80%, 95% or about 100% of the cells in the suspension are megakaryocytes.

The use of a mixer may further be advantageous for ensuring a good homogeneity of the suspension, which is entering into the production chamber of the fluidic device, in particular if the production chamber comprises several channels. Cell mixer may be for instance of the type disclosed by Stroock et al. ("Chaotic Mixer for Microchannels", *Science*, vol. 295, no 5555, p. 647-651, 2002).

At the outlet of the production chamber, the outflow contains produced platelets but it may further contain naked nuclei and/or intact megakaryocytes. A means for separating the produced platelets may be thus advantageously put downstream of the production chamber. Conventional cell sorter device may be used, such as those fitted for microfluidic techniques or for large volumes like apheresis techniques. The platelet sorter may be selected from the group consisting of a cross-flow filtration device, a laminar-flow-based cell sorter, a dielectrophoresis-activated cell sorter, an optical force-based cell sorter, a magnetic force-based cell sorter, and acoustic force-based cell sorter and an inertial forces-based cell sorter. Among the laminar-flow-based cell sorters, the device may be a cell sorter based on the pinched-flow fractionation technique, as disclosed for example by Takagi et al. ("Continuous particle separation in a microchannel having asymmetrically arranged multiple branches", *Lab Chip*, vol. 5, no 7, p. 778, 2005) or based on the Deterministic Lateral Displacement, as described for example by L. R. Huang et al. ("Continuous Particle Separation through Deterministic Lateral Displacement", *Science*, 304, 987, 2004).

The invention is further directed to an ex vivo method for producing platelets from megakaryocytes or their fragments. Said method is carried out by using the fluidic device according to the invention as disclosed above. All particular features and embodiments disclosed above for the fluidic device are thus features and embodiments of the method.

First, the method comprises the step of introducing a suspension of megakaryocytes or their fragments into the fluidic device according to the invention. The flow said suspension may be generated and controlled by a pump optionally coupled with a flow rate controller. Typically, each channel of the production chamber defines a single flow, allowing the suspension of megakaryocytes or their fragments to flow from its inlet to its outlet through the production chamber. Accordingly, the flow is directed from the channel inlet to the channel outlet. According to a preferred embodiment, the flow introduced into the fluidic device is continuous.

As disclosed above, the suspension of megakaryocytes may be a suspension isolated from a donor or obtained by differentiation of progenitor cells, for example progenitor cells selected from the group consisting of hematopoietic stem cells, embryonic stem cells and induced pluripotent stem cells.

In the fluidic device, the suspension of megakaryocytes or their fragments is brought to the production chamber. According to a preferred embodiment, prior to entering in the production chamber said suspension is sorted using the cell sorter and/or homogenized. The homogenization may be carried out in a mixer upstream from the production chamber. Then, the suspension of megakaryocytes or their fragments is brought at the inlet of one or more channels in the production chamber.

After its introduction, the suspension of megakaryocytes or their fragments is subjected to a flow under shear rate suitable for elongation, fragmentation of the megakaryocytes and platelet release in the channel of the production chamber.

As used herein, the term "wall shear rate" ($\dot{\gamma}_w$) refers to the parameter used to characterize the interaction of the flow with the surface of the channel, the obstacles or the megakaryocytes.

The wall shear rate $\dot{\gamma}_w$ is defined at any local surface element. On a specific surface element can be defined a normal vector $\hat{n}$ and a vector $\hat{m}$ tangential to the surface and in the local direction of the fluid velocity $\hat{v}$ so as ($\hat{n}$, $\hat{m}$) is a planar Cartesian coordinate system. The wall shear rate is then defined by $$\frac{\partial \hat{v} \cdot \hat{m}}{\partial n}.$$

The SI unit of measurement for shear rates is $s^{-1}$.

The value of the wall shear rate will change locally because of the size, shape and place of the obstacles. Consequently, in the textured portion of the channel of the device according to the invention, the suspension of megakaryocytes or their fragments is subjected to a flow under a shear rate $\dot{\gamma}$, which varies between a minimum value $\dot{\gamma}_{min}$ and a maximum value $\dot{\gamma}_{max}$.

According to a preferred embodiment of the invention, the flow rate may be fixed within a range value enabling to subject said megakaryocytes in the textured portion of the channel to a wall shear rate $\dot{\gamma}_w$ ranging from 0 to a maximum value $\dot{\gamma}_{max}$, preferably not exceeding 30,000 $s^{-1}$, preferably 10,000 $s^{-1}$, more preferably 8,000 $s^{-1}$ and even more preferably 5,000 $s^{-1}$.

The shear rate $\dot{\gamma}_w$ in the textured portion of the channel of the device according to the invention may be numerically calculated using the finite element method, for a given channel geometry, suspension liquid phase parameters and flow rate.

By comparison, in the human circulation, the wall shear rates vary from 30-40 $s^{-1}$ in the largest veins to 5000 $s^{-1}$ in the microcirculation.

At the outlet of the channel, the collected suspension contains produced platelets. According to an aspect of the invention, the collected suspension at the outlet of the channel may further contain naked nuclei and/or intact megakaryocytes. Consequently, the method may further comprise a step of purifying, enriching or separating platelets from said suspension. In addition, said platelets may be sorted out at the outlet of the channel. The sorting may be carried out with a cell sorter downstream of the production chamber, as disclosed above. For instance, the sorting may be carried out by a method selected from the group consisting of cross-flow filtration, laminar flow-based sorting, dielectrophoresis-based sorting, optical force-based sorting, magnetic force-based sorting, acoustic force-based sorting or inertial forces-based sorting.

Advantageously, the fluidic device of the invention makes it possible to produce platelets from a suspension of megakaryocytes with a high yield production while maintaining the functional qualities of the newly generated platelets.

Platelets obtained by the method described may be used for the preparation of a pharmaceutical composition, for example for the treatment of decreased platelet count disorders, in particular thrombocytopenia and thrombocytopathy. For example, the platelets obtainable by the method according to the invention may be transfused in an efficient amount to a subject suffering of a disorder of platelet production.

Moreover, the method of the invention for producing platelets is suitable to large-scale production of high quality and standardized platelets. Consequently, produced platelets may be used for diagnostic purposes. They can be used as a normal control for the standardization of platelet function. Indeed, platelet function testing requires fresh blood platelets in native functional condition from normal individuals and affected individuals. Standardization of platelet function testing requires that the laboratory should perform a normal control with every batch of platelet function tests performed. However continuous regular blood sampling by venepuncture raises several health concerns and ethical issues. Advantageously, platelets obtained by the method of the invention may be used as a positive control in an in vitro diagnostic test for measuring platelet function.

This invention will be further understood in light of the following non-limiting examples, which are given for illustration purposes only, and also in connection with the attached drawing in which:

DESCRIPTIONS OF THE DRAWINGS

Figure 3:
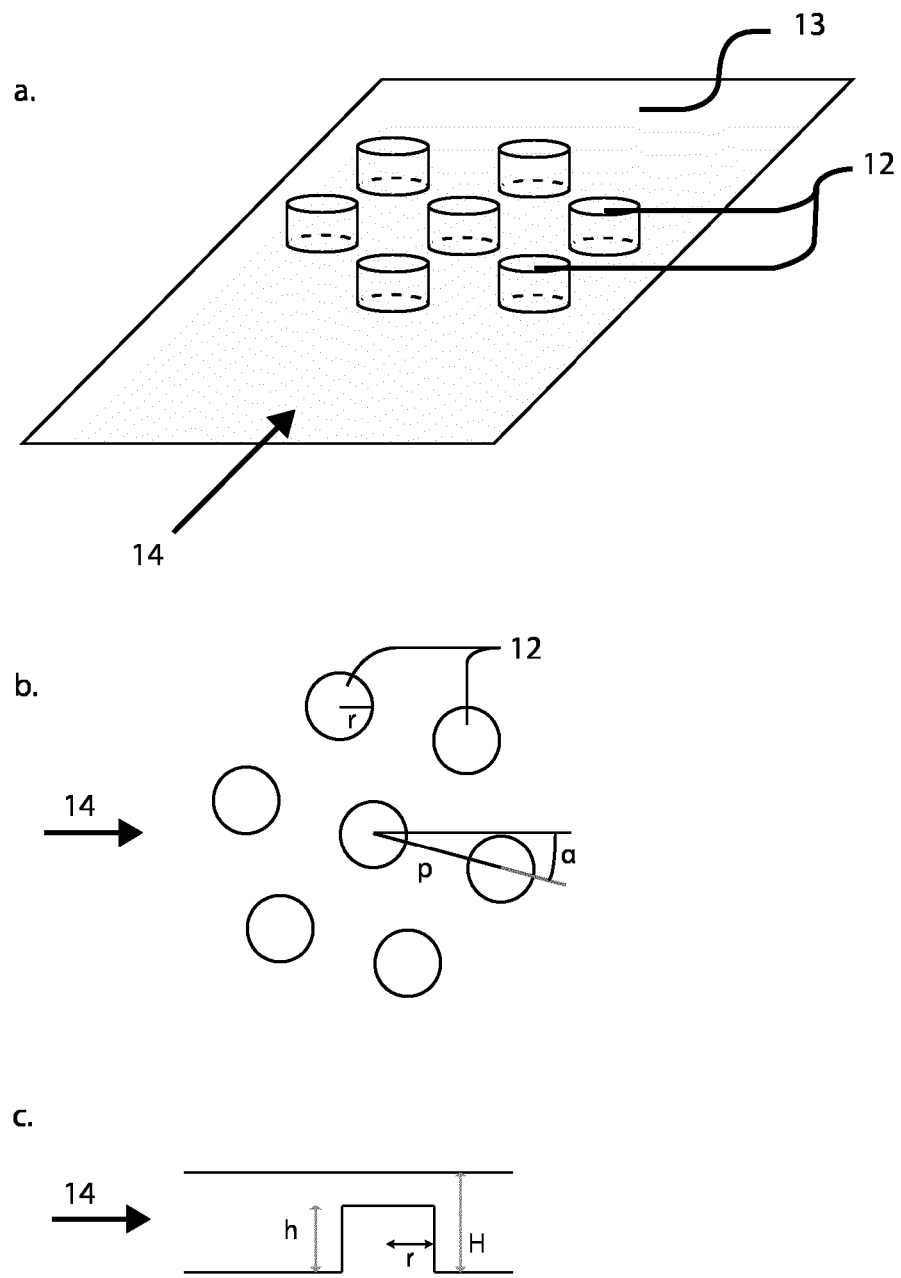

FIG. 3 schematically represents a textured surface with obstacles having a post shape. FIG. 3.a is a perspective view. FIG. 3.b is a top view. FIG. 3.c is a cross-section view.

Figure 4:
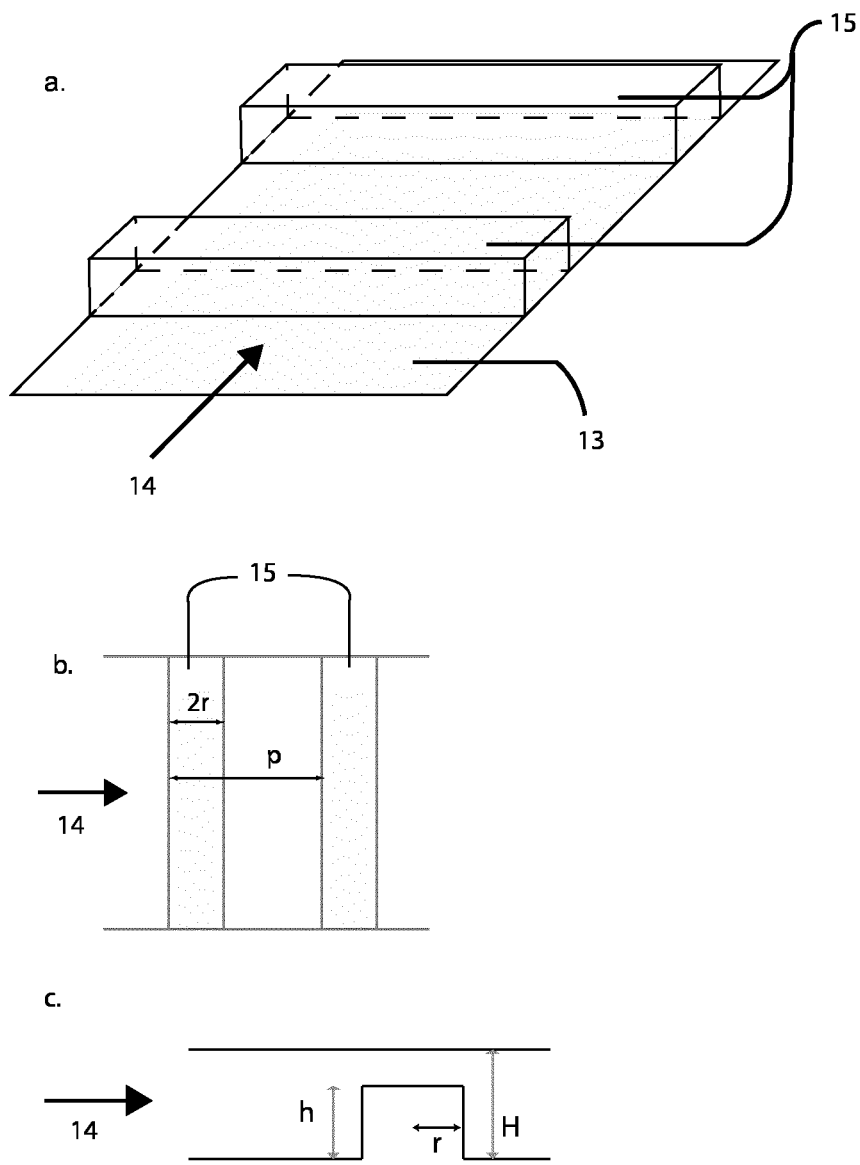

FIG. 4 schematically represents a textured surface with obstacles having a beam shape. FIG. 4.a is a perspective view. FIG. 4.b is a top view. FIG. 4.c is a cross-section view.

Figure 5:
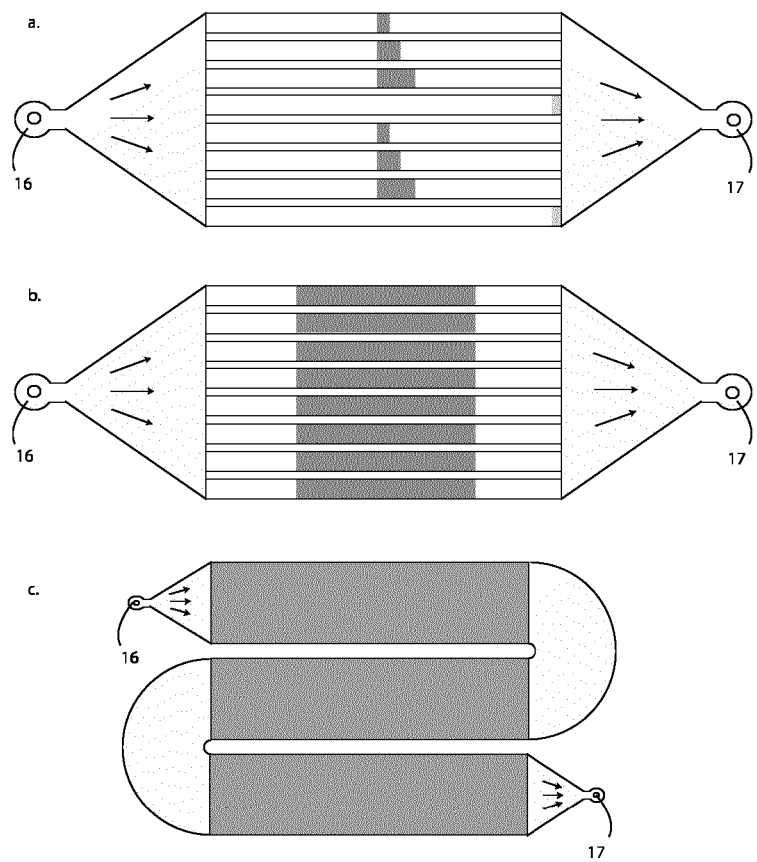

FIG. 5 represents three different channel geometries used in the example: "channel geometry 1" on FIG. 5.a, "channel geometry 2" on FIG. 5.b and "channel geometry 3" on FIG. 5.c.

Figure 6:
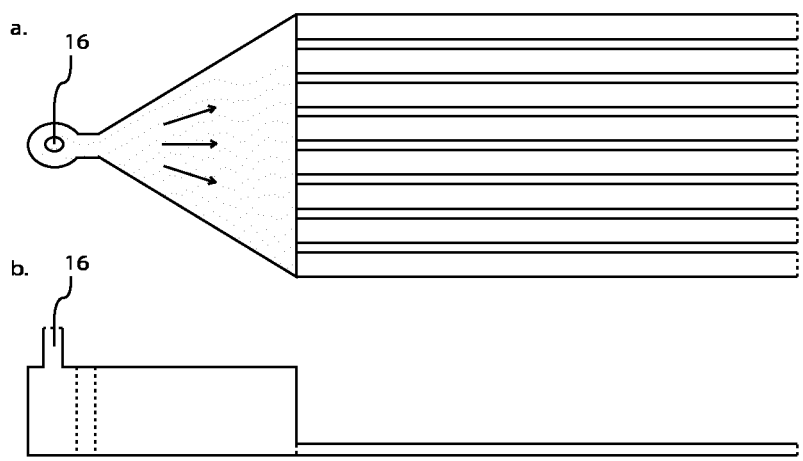

FIG. 6.a is a top view and FIG. 6.b cross-section view of the cell distribution upstream from the parallelized channels used in the example.

Figure 7:
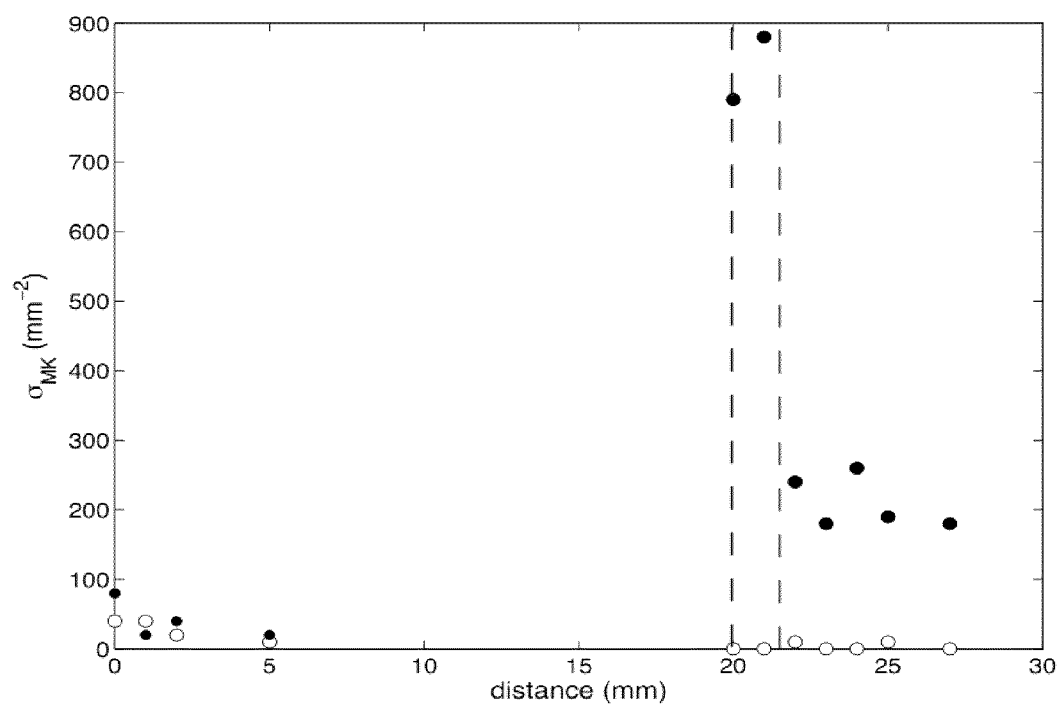

FIG. 7 is a graph representing the effect of the textured surface on the megakaryocyte capture. Empty circles correspond to the density σ of adherent megakaryocytes in a non-textured channel, while plain circles correspond to the density σ of adherent megakaryocytes in a channel textured between the dashed lines. The texture corresponds to a geometry defined by r=15 μm, p=85 μm, H=34 μm and h=20 μm. The x axis represents the distance from channel inlet. The images were recorded 50 min after the beginning of the experiment.

Figure 8:
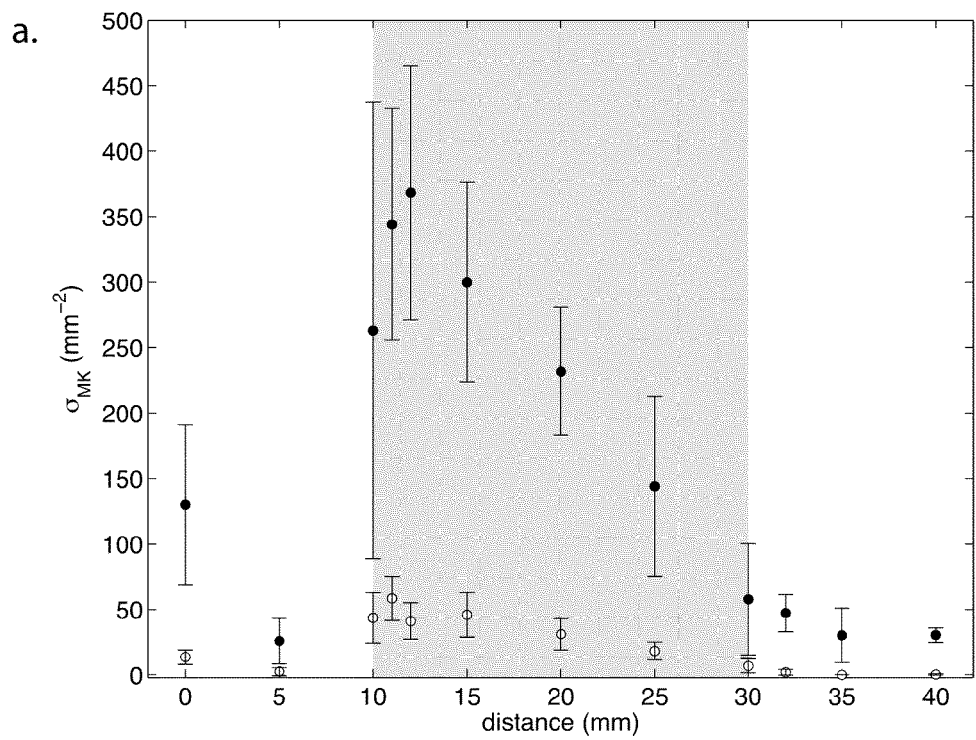
Figure 8:
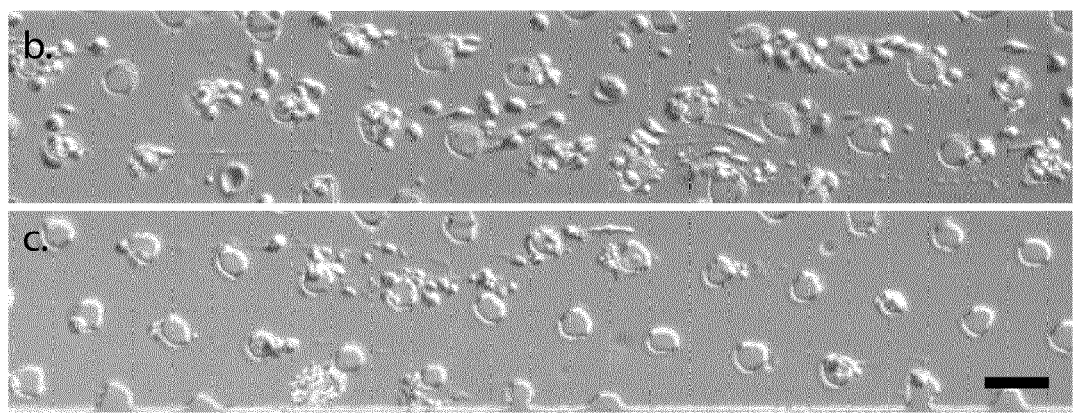

FIG. 8 illustrates the effect of VWF on the cell capture. (a) Surface density σ of adherent megakaryocytes for eight different experiments alternatively made with VWF (plain circles) and BSA (empty circles) surface coating of the channels. The x axis represents the distance from channel inlet. The count is made for each experiment after 50 min of perfusion. The grey zone represents the textured part of the microchannel. (b) Typical image of the surface after 50 min of perfusion when using a VWF coated microchannel. (c) Typical image of the surface after 50 min of perfusion when using a BSA coated microchannel. The scale bar represents 80 μm.

Figure 9:
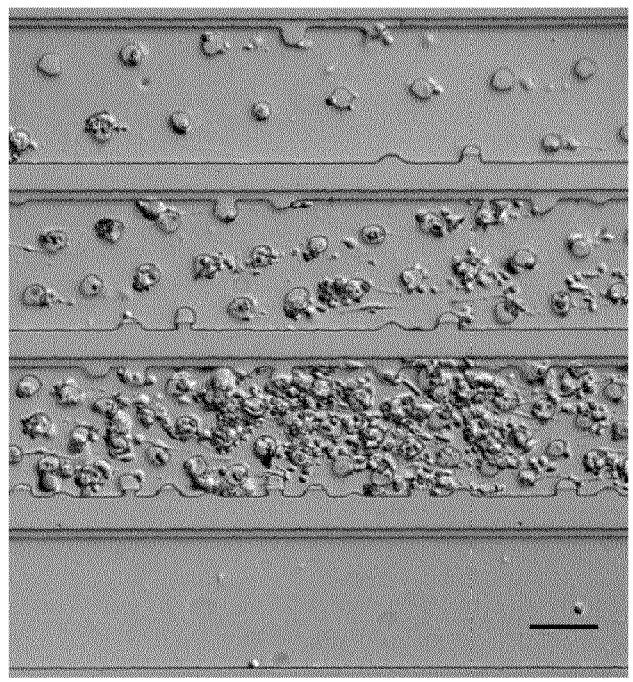

FIG. 9 is an image illustrating the effect of the plot density on the adherent megakaryocytes surface density in geometry 1, with r equals to 15 μm. The different channels are respectively patterned with p equals to 120 μm, 85 μm and 60 μm. The last channel is a negative test. The image is taken after 50 min of experiment. We observe important aggregation of megakaryocytes when decreasing p under a certain threshold as it is the case in the present example for p=60 μm. The scale bar represents 100 μm.

Figure 10:
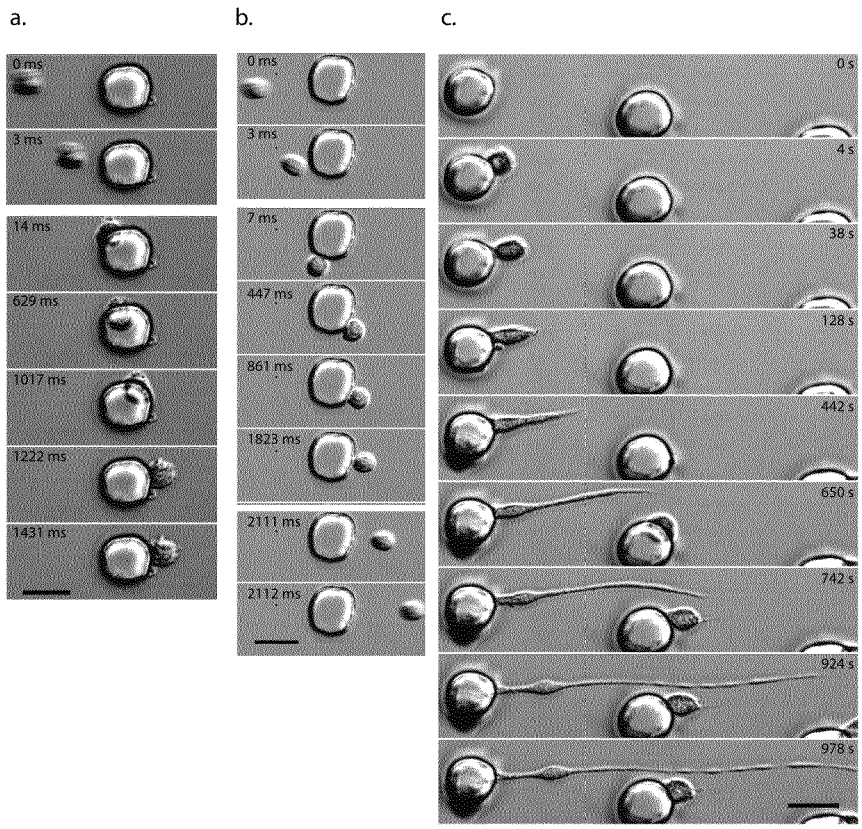

FIG. 10 is images illustrating different behaviors of the megakaryocytes towards the post array. (a) Capture of a megakaryocyte from advection to translocation on the planar surface of the post. The sequence shows two different time scales and transport behaviors. From 0 ms to 3 ms, the megakaryocyte is advected by the flow yielding a speed of several mm·s$^{-1}$. From 14 ms to 1431 ms, the megakaryocyte translocates on the planar surface of the post, yielding a speed of several μm·s$^{-1}$. (b) Capture of a megakaryocyte on the rounded surface of a post. The sequence shows two transport behaviors: the megakaryocyte is advected to the post from 0 ms to 3 ms, then translocates on the post rounded surface from 7 ms to 1823 ms and is finally released in advection from 2111 ms. (c) A megakaryocyte is captured by the planar surface of the post and is trapped at its right side. We observe from 4 s to 978 s the elongation of the megakaryocyte, forming a beads-on-a-thread-like structure. The scale bar represents 30 μm.

Figure 11:
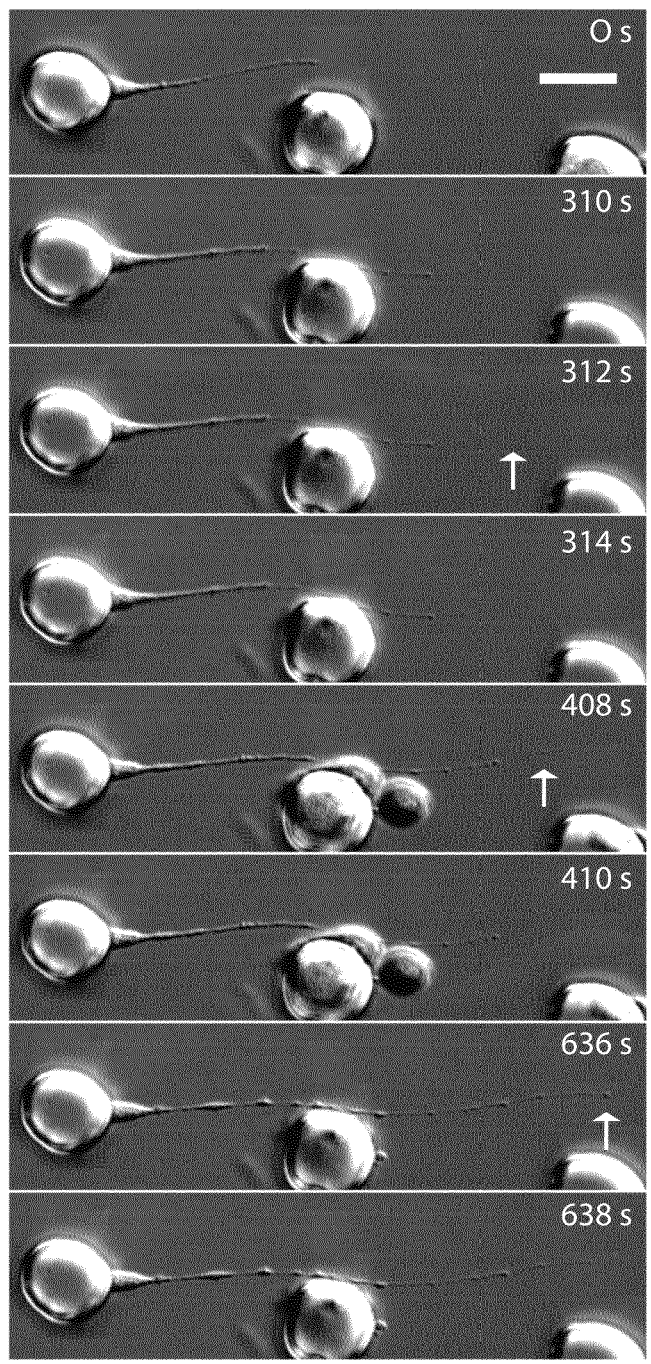

FIG. 11 is an image illustrating the elongation and fragmentation of a mature megakaryocyte. The time montage shows a trapped megakaryocyte with a beads-on-a-thread-like structure undergoing three ruptures of the elongated structure. Each white arrow shows the part of the elongation to be released in advection, as it disappears on the following images. The scale bar represents 30 μm.

Figure 12:
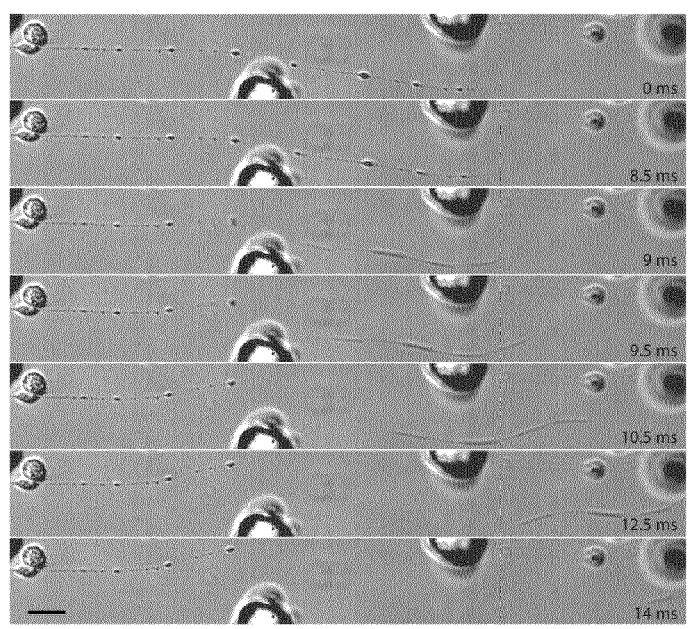

FIG. 12 is an image illustrating a detail of the platelet release. The time montage shows a trapped megakaryocyte with an elongated beads-on-a-thread-like aspect. The rupture happens between 8.5 ms and 9 ms. The megakaryocyte remains trapped (left side) and the released proplatelet is dragged by the flow. The scale bar represents 20 μm.

Figure 13:
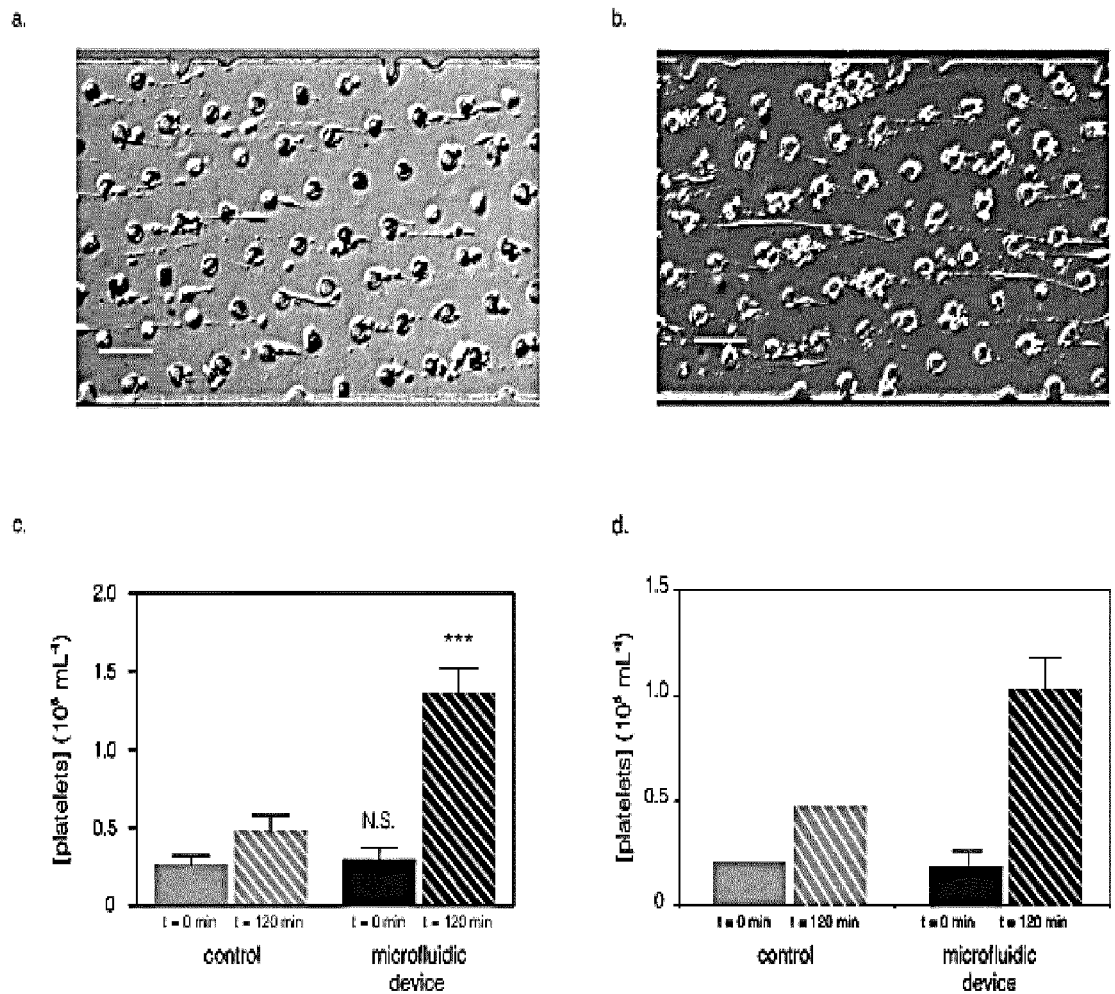

FIGS. 13 a and b is a picture illustrating an example of a large-scale platelet production from elongating megakaryocytes simultaneously trapped onto a large number of posts Image illustrating a detail of a single channel enabling a two dimension parallelization of the platelet shedding process from mature megakaryocytes originating from (a) cord blood hematopoietic stem cells and (b) peripheral blood hematopoietic stem cells. Notice the longer elongations covering the whole field of observation in the latter case. The scale bar represents 100 μm. FIGS. 13 c and d represents quantitative evaluation of platelet production in the microfluidic device. Comparison of platelet production during 2 hours in the microfluidic device vs control, from mature megakaryocytes originating from (c) cord blood hematopoietic stem cells and (d) peripheral blood hematopoietic stem cells. In this experiment, a megakaryocyte suspension circulates in a closed-loop circuit through tubings into five parallel microfluidic chips (microfluidic device). A control megakaryocyte suspension circulates in a closed-loop circuit through tubings without microfluidic chip (control). Platelet concentrations are obtained by counting in a hemocytometer. (c) Means±SEM (n=5) for microfluidic device (black bars) vs control (light grey bars), at the beginning of the experiment (plain bars, t=0 min) and at the end of the experiment (hatched bars, t=120 min), are provided. Statistical analysis was performed using Student t-test for paired samples of platelet concentrations in the microfluidic device vs control and p values obtained at t=120 min denote a significant difference (***$p<0.005$). (d). Means±SEM (n=3) for microfluidic device (black bars) vs control (n=1) (light grey bars), at the beginning of the experiment (plain bars, t=0 min) and at the end of the experiment (hatched bars, t=120 min), are provided.

Figure 14:
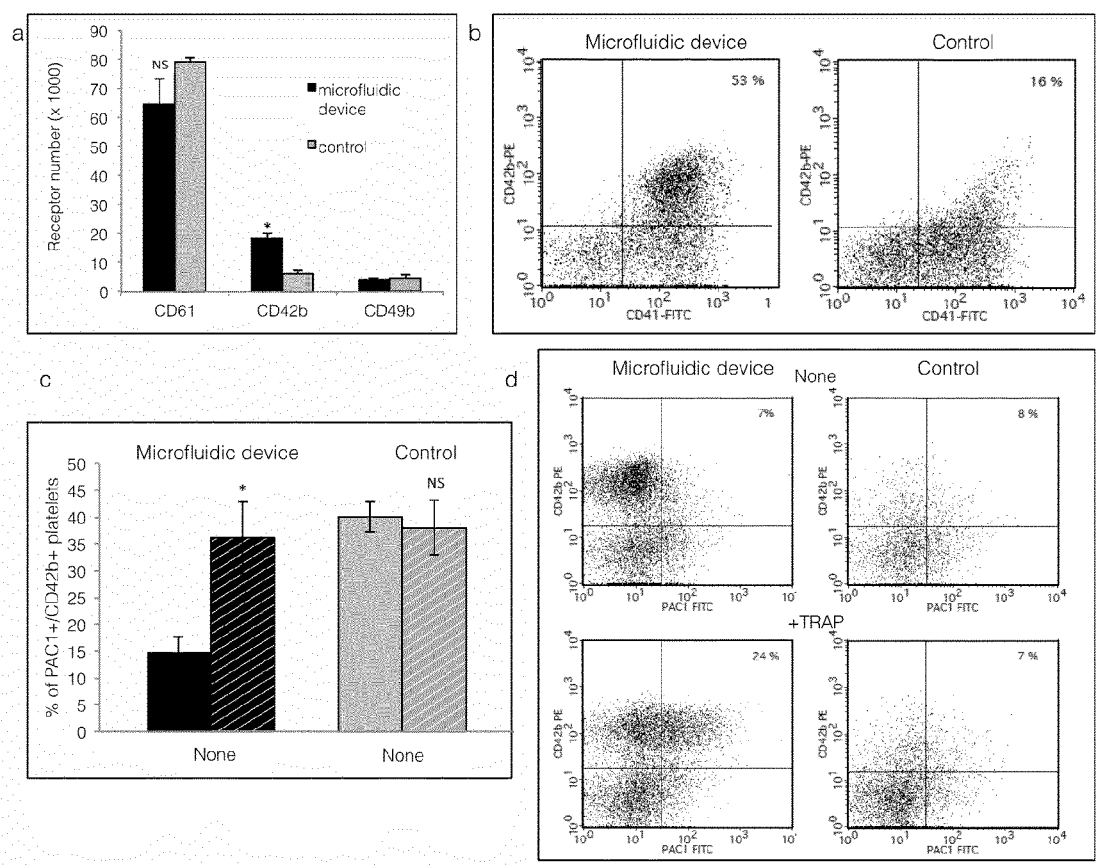

FIG. 14 is a picture showing flow cytometry analysis of platelets produced in the microfluidic device by comparison with those obtained in a control system devoid of microfluidic chips, as described in details in the legend of FIG. 13.c above.

(a) Single color flow cytometry analysis of platelet receptors, indicating the number of CD61, CD42b and CD49b receptors on the surface of platelets produced in the microfluidic device (black bars) and the control (light grey bars). Means±SEM (n=3) are provided and statistical analysis was performed using Student t-test for unpaired samples comparing receptor numbers in the microfluidic device vs control. The asterisk for CD42b histograms denotes a significant difference ($p<0.05$).

(b) Two-color flow cytometry analysis of platelet receptors, indicating the population of $CD41^+CD42b^+$ platelets produced in the microfluidic device vs the background values in the control.

(c and d) Two-color flow cytometry analysis of platelet receptors without or with activation of the CD41/CD61 receptor by the agonist peptide SFLLRN that stimulates the human PAR-1 thrombin receptor (TRAP). In FIG. 14.c, histograms indicate, within the platelet and $CD42b^+$ gate, the % of PAC-1 positive elements before (plain bars) or after (hatched bars) TRAP activation of platelets produced in the microfluidic device (black bars) and the control (light grey bars). Means±SEM (n=6) are provided and statistical analysis was performed using Student t-test for unpaired samples comparing non stimulated platelets vs TRAP-stimulated platelets. The asterisk for p values denotes a significant difference (p<0.05) between the % of PAC-1 positive elements before or after TRAP activation of platelets produced in the microfluidic device, but not in the control. FIG. 14.d displays the corresponding dot plots within the platelet gate, indicating the population of PAC1$^+$CD42b$^+$ platelets in the non stimulated (upper panels) and TRAP stimulated samples (lower panels) produced in the microfluidic device (left panels) vs control (right panels). Notice the shift of the PAC1$^+$CD42b$^+$ population in the TRAP stimulated platelets produced in the microfluidic device that is absent from the control.

Figure 15:
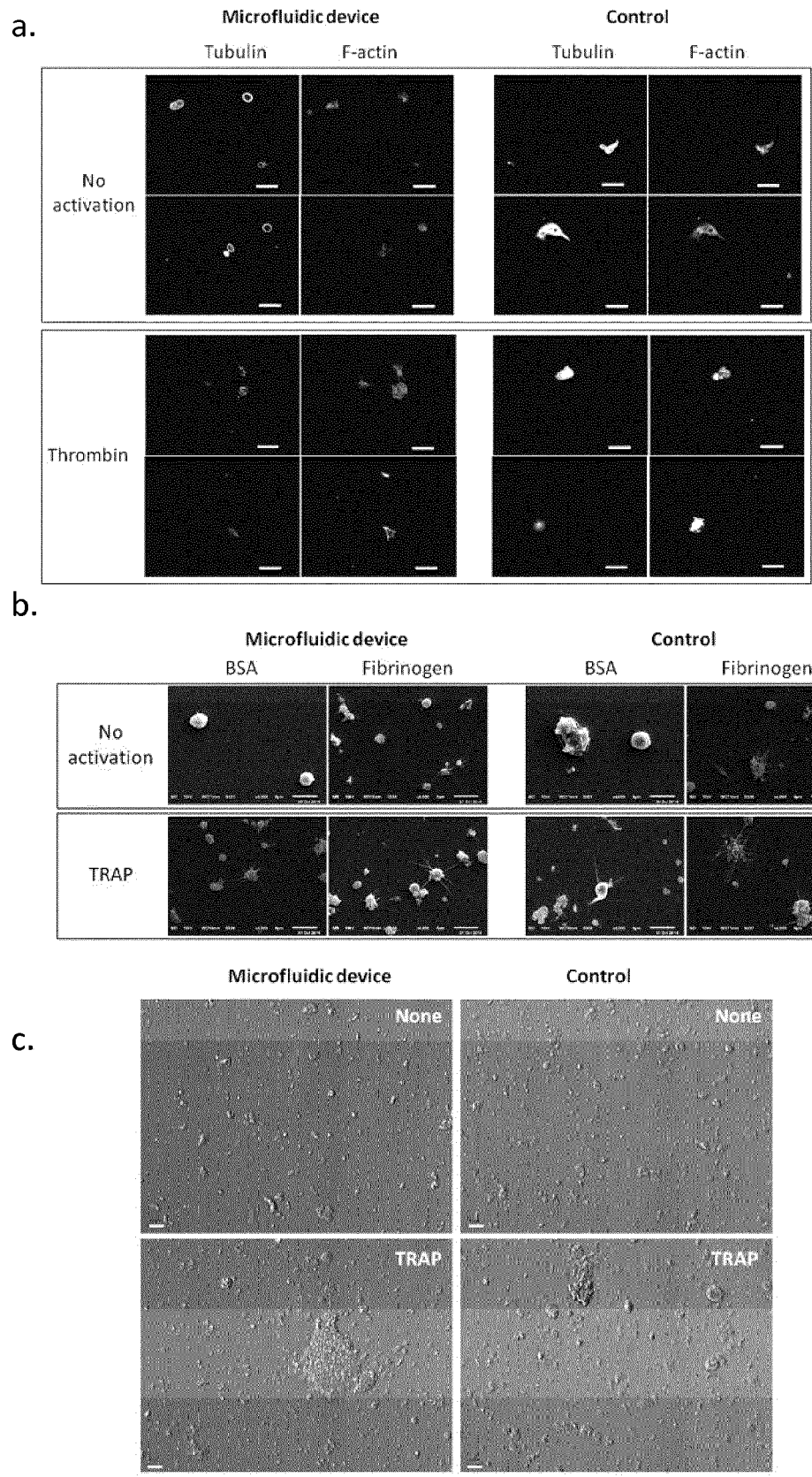

FIG. 15 is a picture showing microphotographs of adhesion and aggregation of platelets produced in the microfluidic device by comparison with those obtained in a control system devoid of microfluidic chips, as described in details in the legend of FIG. 13.c above.

(a) Indirect immunofluorescence labeling with anti-tubulin antibodies, revealed by a secondary AlexaFluor488 anti-mouse antibody and AlexaFluor546 phalloidin for F-actin staining is performed in the absence (top panels) or presence of thrombin (bottom panels) in samples produced by the fluidic device (left panels) or the control (right panels). Image acquisition was performed with an Axio Observer microscope (Zeiss) at 40×1.6-fold magnification with a QIClick-F-CLR-12 Digital CCD Camera (Q Imaging). Circular tubulin staining, characteristic of unactivated platelets is seen in the samples collected at the exit of the fluidic device (top left), whereas larger fragments without circular tubulin staining are recovered in samples collected from the control (top right). Actin stress fibers characteristic of activated platelets are seen in the samples collected at the exit of the fluidic device (bottom left), whereas larger elements without organized stress fibers staining are recovered in samples collected from the control (bottom right). Platelets are adherent to fibrinogen. The scale bar represents 5 µm.

(b) Scanning electron microscopy images of platelets or elements recovered at the exit of the fluidic device (top left) and in samples collected from the control (right) in the absence (top panels) or presence of activation by agonist peptide SFLLRN that simulates the human PAR-1 thrombin receptor TRAP-1 (bottom panels). Each condition includes either adhesion to bovine serum albumin or fibrinogen. The scale bar represents 5 µm.

(c) Aggregation in the presence of fibrinogen and $CaCl_2$. Platelet aggregates are observed before (upper panels) or after activation with the agonist peptide SFLLRN that simulates the human PAR-1 thrombin receptor TRAP-1 (lower panels). Large aggregates are visible in the sample collected at the exit of the fluidic device (lower left panel). Fragments recovered in the control samples do not aggregate in the presence of the agonist peptide (lower right panel). The scale bar represents 10 µm.

Figure 16:
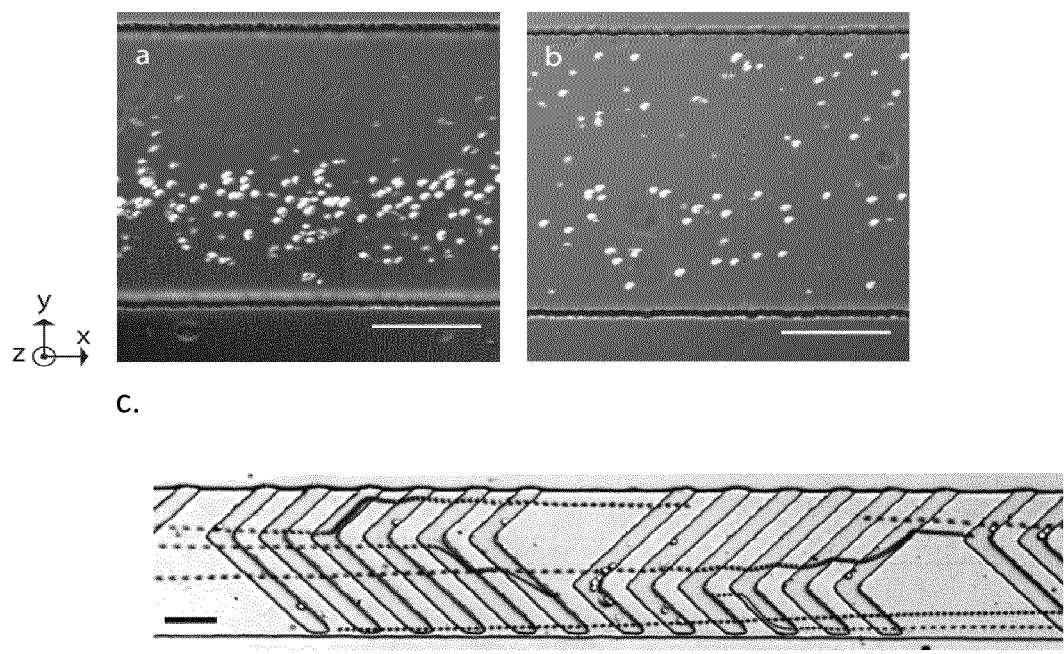

FIG. 16 include pictures showing mature megakaryocytes suspension introduced into the microfluidic mixer. (a) Superposition of 400 pictures taken at the inlet of the micro mixer. The cells are flowing in advection through the x direction from left to right and are focalized towards the y-axis. (b) Superposition of 400 pictures at the outlet of the micro mixer. Cells flow is homogeneous towards the y direction. (c) Trajectories of mature megakaryocytes in the mixer. Superposition of 200 consecutive pictures separated by 1 ms. The scale bar represents 100 µm.

Figure 17:
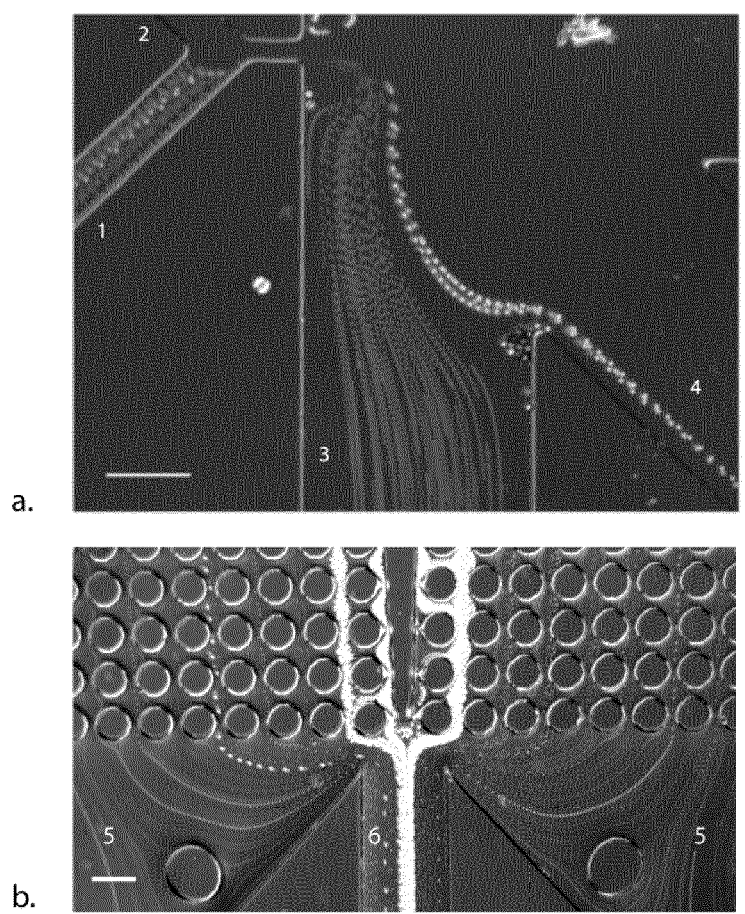

FIG. 17 shows two examples of cell sorter. FIG. 17.a is a picture showing platelet sorting by pinched flow fractionation. The inlet cell suspension is composed of both fixed platelets and DAMI cells. The mixture is introduced in channel (1). Cell-free buffer is introduced in channel (2). Platelets are recouped out of the channel (3) as DAMI cells are recouped out of channel (4). The image is a superposition of 30 consecutive images separated by 1 ms to show the different cell trajectories. The scale bar represents 200 µm. FIG. 17.b is a picture showing platelet sorting by Deterministic Lateral Displacement. The inlet cell suspension is composed of both fixed platelets and DAMI cells. The mixture is introduced at the entrance and sorted at the exit (shown on the image): the DAMI cells are deflected and sorted in the central outlet (5) whereas the platelets are not deflected and sorted on the lateral outlets (6). The image is a superposition of 485 consecutive images separated by 0.3 ms to show the different cell trajectories. The scale bar represents 100 µm.

Figure 1:
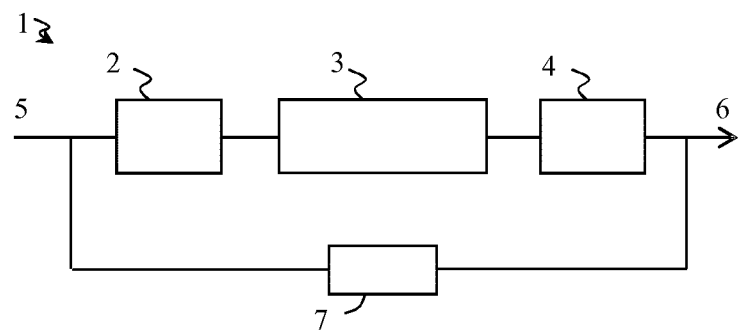
FIG. 1 is a scheme of one embodiment of a platelet production fluidic device according to the invention.

In FIG. 1, a fluidic device 1 is represented schematically. The fluidic device 1 is composed of a lateral cell mixer 2, a production chamber 3 and a cell sorter 4, in series. The suspension of megakaryocytes 5 is introduced in the fluidic device 1. The outflow suspension 6 is collected. A flow rate controller 7 is implemented between the inflow suspension 5 and outflow suspension 6. The flow rate can be imposed by a pressure difference or a flow rate source, for instance syringe pump in an open system, peristaltic pump in a closed-loop system (not shown).

Figure 2:
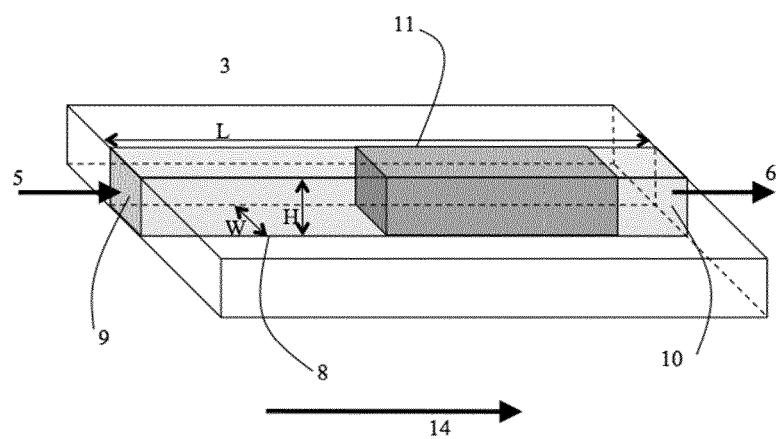
FIG. 2 illustrates one embodiment of a production chamber of a fluidic device of the invention.

The production chamber 3 of a fluidic device is represented with more details in FIG. 2. The production chamber 3 comprises one channel 8 with two openings 9, 10: one inlet 9 for the introduction of the suspension of megakaryocytes 5 and one outlet 10 for the collection of the outflow suspension 6. The longitudinal direction of the channel is represented by the arrow 14. The channel 8 has a length L, a width W and a height H. According to the invention, the channel 8 is textured on at least one of its inner surface.

The texturing of the surface is created by a plurality of obstacles placed in the inner surface of at least a portion of the channel.

According to one preferred embodiments, the obstacles are posts and are organized as shown in FIG. 3. The posts 12 are placed on the inner surface of one channel wall 13. Each post 12 has a substantially circular section of a radius r, and said posts are arranged to form a regular pattern with a hexagonal periodic structure. The closest distance between two post centers is represented by p. The angle α is the lowest angle defined by the longitudinal direction of the channel 14 and one of the lattice vectors of the primitive cell of the hexagonal periodic structure. The height of the posts is represented by h, which is such as 0<h≤H, wherein H is the height of the channel.

According to another preferred embodiments, the obstacles are beams and are organized as shown in FIG. 4. The beams 15 are placed on the inner surface of one channel wall 13. Each beam 15 has a substantially rectangular section with a height h and a width 2r. The length of the beams is equal to the length of width W of the channel. The beams are placed perpendicularly to the longitudinal direction of the channel 14. The closest distance between the centers of two beams is represented by p. The height of the beams is represented by h, which is such as 0<h≤H, wherein H is the height of the channel.

EXAMPLES

Material and Methods
CD34+ Cells Culture and Differentiation

CD34+ cells were isolated from human umbilical cord blood (UCB) or peripheral blood by an immunomagnetic technique (Miltenyi Biotec, Paris, France) as previously reported (see Poirault-Chassac et al, "Notch/Delta4 signaling inhibits human megakaryocytic terminal differentiation", *Blood*, vol. 116, no 25, p. 5670-5678, 2010). These blood samples were obtained after informed consent and approval from our Institute Ethics Committee and in accordance with the Declaration of Helsinki. CD34+ cells were cultured at 37° C. in 5% $CO_2$ in complete medium consisting of Iscove modified Dulbecco medium (IMDM; GibcoInvitrogen, Saint-Aubin, France) supplemented with 15% BIT 9500 serum substitute (Stem Cells Technologies, Grenoble, France), α-monothioglycerol (Sigma-Aldrich, Saint-Quentin Fallavier, France) and liposomes (phosphatidyl-choline, cholesterol and oleic acid; SigmaAldrich). Human recombinant stem cell factor (SCF, 10 ng/mL; Miltenyi Biotec) and thrombopoietin peptide agonist AF13948 (TPO, 50 nM) (see Dunois-Lardé et al, "Exposure of human megakaryocytes to high shear rates accelerates platelet production", *Blood*, vol. 114, no 9, p. 1875-1883, 2009) were added once at day 0 to the culture medium followed by addition of 20 nM TPO without SCF at day 7. Mature UCB megakaryocytes obtained after 12-14 days of culture were diluted in complete medium to a concentration of 0.7-1.2×10⁶ mL, thus approximately 10-fold less concentrated than in previously reported experiments. Measured mean diameter $D_{cell}$ was found to be 12.5+/−1.7 µm. Removal of platelets formed during culture and immediately prior to shear exposure was performed by means of a BSA gradient according to the methods reported in (Robert A, Cortin V, Garnier A, Pineault N. Megakaryocyte and platelet production from human cord blood stem cells. *Methods Mol Biol*. 2012; 788: 219-47). The concentration was then adjusted to 200 000 megakaryocytes/mL. Results are with megakaryocytes derived from UCB CD34+ unless specified otherwise.

System Architecture

A suspension of mature megakaryocytes is introduced in a 25 cm² flask (Corning, USA) fixed on an orbital mixer (IKA MS3 basic), rotating at least at 300 rpm. The orbital mixer is used to maintain the homogeneity of the cell concentration in the suspension. The megakaryocytes concentration range in the flask is at least 100 mL⁻¹ and cannot exceed 10×10⁶ mL⁻¹.

Many methods can be used to control the flow through the different components: a differential pressure controller, a syringe pump and a peristaltic pump for example. When using a differential pressure control, an air pressure inlet and a suspension outlet are hermetically plugged into the cork of the flask. The air pressure is imposed in the flask by a pressure controller (MFCS-4C, Fluigent S.A., France). The flask is connected to the inlet of the microfluidic chip with Polyether ether ketone (PEEK) tubing (Upchurch Scientific, USA). Other tubing can be used (Tygon R-1000, Saint-Gobain, France, PTFE tubing, Saint Gobain, France for instance). The suspension is collected at the outlet. When using a peristaltic pump (Reglo, Ismatec, Switzerland), both inlet and outlet tubing arrive in the same rotating flask. The peristaltic pump can be plugged upstream or downstream from the microfluidic components. The megakaryocyte suspension flow can also be imposed by a syringe pump (PHD 2000, Harvard apparatus, US).

Three microfluidic components are implemented in series: a megakaryocyte sorter and/or a lateral cell mixer upstream, a platelet production channel, and a cell sorter downstream, as depicted in FIG. 1. Cell mixer and cell sorter are optional.

Devices Fabrication

Microfluidic components were made following a soft lithography rapid prototyping (Xia et al. 1998. "Soft lithography". *Annual Review of Materials Science*. vol. 28, no 1, p. 153-184). First, transparencies were produced from a computer assisted design file containing the design of microchannels. These transparencies were used as masks in transferring the pattern into negative photo resist (SU-8 2000 and 3000 series, Microchem, US) by conventional photolithography, yielding a master with positive relief of micro channels. Both channels were made from molded polydimethylsiloxane (PDMS, Sylgard, Dow Corning, USA), sealed on glass slides. PDMS prepolymer and curing agent were mixed and degassed. The mixture was poured onto the master, cured for 2 h at 70° C., cut into individual chips, and inlet and outlet holes were punched. Glass slides were cleaned with isopropanol and dried. Both PDMS individual structures and glass slides were treated in an oxygen plasma oven and then sealed.

Platelet Production Channels

The textured surface is defined by 3D patterns on the channel walls (glass or PDMS). Herein we present two examples of these possible patterns: a hexagonal array of disks in the (Oxy) plane and a 1D array of beams in the (Ox) direction. The geometries of those patterns are described in FIG. 3 and FIG. 4. The design of the post array is defined by three parameters: the disk radius r, the distance between two disk centers p and the angle α between the direction of the flow at the inlet and the direction defined by two pillar centers. In the geometries we used for the experiments herein, α was defined by the following criterion: sin α=r/p. This criterion geometrically implies that two neighbor disk centers, once projected on an axis normal to the initial flow direction, are separated by one radius. Experimentally, r varied from 15 µm to 20 µm and p varied from 60 µm to 120 µm. FIG. 3.c and FIG. 4.c show the profile of an obstacle (beam or post) in the (Oxz) plane. The height of the channel and the height of the obstacle are defined, respectively by H and h. The parameter h/H was experimentally varied between 0.22 (small posts) and 1 (full pillars).

Three different channel geometries were used in this example, illustrated in FIG. 5.a, FIG. 5.b and FIG. 5.c:

The first one, so-called "channel geometry 1", was used to measure the influence of the channel texture on megakaryocyte capture. It is composed of 8 parallel channels: 6 textured channels and two smooth channels. From x=0 mm (inlet) to x=20 mm (part 1) all channels are smooth. The patterns followed the parameters r=15 µm, H=36 µm, h/H=0.55. p varied for the different textured channels: p=60 µm (2 channels), p=85 µm (2 channels) and p=120 µm (2 channels). All the hydraulic resistances were made equal by varying the texture length for the different p parameters. For p=85 µm, the channels were textured between 20 and 22 mm and then smooth from 22 to 40 mm.

The second one, so-called "channel geometry 2", is used to measure the protein surface coating effects and the texture effects. It is composed of 8 parallel channels. All the channels were four centimeters long and were only textured between the first and the third centimeter.

Channel geometry 2 is patterned with the parameters r=15 μm, H=36 μm, h/H=0.55 and p=85 μm.

The third one, so-called "channel geometry 3", is used to parallelize the platelet production process using obstacles effects. It is composed of 8 parallel channels in serpentine shape (shown as a block in FIG. 5.*c*). All the channels were 17.3 cm long and textured on the straight parts of the channels, representing 77% of the total length. Channel geometry 3 is patterned with the parameters r=15 μm, H=52 μm, h/H=1 and p=85 μm.

Shear Rates

We define a surface element on the channel wall, whatever on glass or PDMS (including PDMS obstacles). On this surface element, we define the unit vector of a plane by the vector acting normal to it, n̂. A unit vector m̂, tangential to the surface and in the local direction of the fluid velocity v, is determined so that (n̂, m̂) is a planar Cartesian coordinate system. The wall shear rate γ̇(in s$^{-1}$) is then defined by $$\dot{\gamma} = \frac{\partial \hat{v} \cdot \hat{m}}{\partial n}.$$

The wall shear rate is controlled by both the flow rate in the device and by the geometry of the device. The hydrodynamic resistance of the entire fluidic system was characterized by imposing pressure differences between the inlet and the outlet, by means of a pressure controller, and by measuring the resulting flow rate (Flowell, Fluigent, France).

Videomicroscopy System

The microfluidic chip was set on the stage of an inverted microscope (DMI6000 B, Leica Microsystems GmbH, Germany). A computer assisted motorized stage control was used to record positions along the channel length. We recorded observation field positions and alternated recording images between them along the experiment time. Differential interference contrast objective was used to record movies and images between 10× and 40×. A CMOS high-speed camera (Fastcam SA3, Photron, USA) was used to record images at frequencies from 0.5 to 1500 Hz.

Surface adherent cells were counted manually from the recorded channel images, and cells in suspension were counted both with a hematocytometer and a coulter counter (Scepter II, Millipore, US) when sampled in bulk.

Protein Surface Treatments

Human von Willebrand factor (VWF) was a gift of Laboratoire Français du fractionnement et des Biotechnologies. It was diluted at 40 μg·mL$^{-1}$ in phosphate buffered saline phosphate buffered saline (PBS) without calcium and magnesium ions (Lonza, Belgium), and perfused in sealed microchannels. We used this surface coating only in the platelet production channel.

Bovine serum albumin (Sigma-Aldrich La Verpilleres, France) was diluted at 40 μg·mL$^{-1}$ in phosphate-buffered saline (PBS) and perfused in microchannels.

For both protein treatments, inlets and outlets of the chips were covered by cover slips. The chips were incubated overnight at 4° C. and washed with PBS before the experiment. VWF adsorption on both glass and PDMS was verified by fluorescence labeling with a primary polyclonal rabbit anti-vWF antibody (Dako, 10 μg·mL$^{-1}$) and with a secondary Alexa fluor 546 polyclonal goat anti-rabbit antibody.

Cell Mixer

The design of the mixer is directly inspired from the herringbone-like structure of the chaotic mixer for microchannels disclosed by Stroock et al. ("Chaotic Mixer for Microchannels", *Science*, vol. 295, no 5555, p. 647-651, 2002). Considering Stroock et al parameters, the cell mixer design was made with h=50 μm, w=300 μm, α=1, p=⅔ or ⅓ and q=0.63 μm.

Parallelization of Platelet Production Channels

A high megakaryocyte flow rate into the device is desired to increase the platelet production number. For a given pattern of obstacles and height of the channel, the cell flow rate can be increased by increasing the channel width. As mechanical constraints of the PDMS channels impose a maximum width over height ratio to avoid channel collapse, we parallelized channels to increase the effective width.

Megakaryocytes were introduced in the platelet production channel by means of tubing. Cells were distributed in the parallel channel through a triangular shaped entrance, which brings the cells to every channel (FIG. 6). For a given channel height, the wall shear rate is inversely proportional to the channel width. Consequently, the wall shear rate is much higher close to the inlet walls than before the entrance of the parallelized channels.

To avoid imposing a wall shear rate that could damage the cells, the distribution channel is fabricated using a higher height than the one used in the parallelized shear channels. The ratio of these two heights is typically between 2 and 20.

Platelet Sorting

Naked nuclei and intact megakaryocytes can be removed from the platelets by sorting in serial the outflow suspension from the platelet production channel, as depicted in FIG. 1. This can be done with microfluidic techniques. Apheresis techniques can also be considered for large volumes. We give two examples of platelet sorting using the pinched-flow fractionation technique (Takagi et al., "Continuous particle separation in a microchannel having asymmetrically arranged multiple branches", *Lab Chip*, vol. 5, no 7, p. 778, 2005) and the Deterministic Lateral Displacement (L. R. Huang et al. "Continuous Particle Separation through Deterministic Lateral Displacement", *Science,* 304, 987, 2004). For the pinched-flow fractionation technique, the device is fabricated using a pinch segment width of 50 μm (FIG. 17). The cell suspension is composed of paraformaldehyde-fixed platelets (from whole blood) and DAMI cells (megakaryotic cell line, Greenberg et al. 1988. "Characterization of a new megakaryocytic cell line: the Dami cell". *Blood.* 72:1968-1977). FIG. 17.*a* shows that DAMI cells and platelets can be fractionated in different outlet branches using this technique. Deterministic Lateral Displacement (DLD) is a passive structure-dependent particle size separation method based on laminar flow through a periodic array of micrometer-scale obstacles. A mixture of DAMI cells and fixed platelets are sorted based on a device first described by L. R. Huang et al. (Science, 304, 987 (2004)) and developed by K. Loutherback et al. (AIP Advances 2, 042107 (2012)). The device is composed of one inlet, an array of posts of spherical shape and two outlets (central and lateral). On FIG. 17.*b*, the device is 5 cm long, 3 mm width and 40 μm in height. The post diameter is 85 μm and the spaces between posts are 15 μm. The post row shifting forms an angle of 0.05 radian. The surface is covered by a BSA coating. The DAMI cells are deflected and sorted in the central outlet (6) whereas the platelets are not deflected and sorted on the lateral outlets (5). The device offers a platelet purity of 100% and a platelet recover yield of 80%. The image is a superposition of 485 consecutive images separated by 0.3 ms to show the different cell trajectories. The scale bare represents 100 μm.

Characterization of Collected Platelets

Platelet production in the microfluidic device of geometry 3 was compared to control samples, consisting of tubings without the microfluidic chips. Expression of CD41 and CD42 antigens was characterized using a flow cytometer BD Fluorescence Activated Cell Sorter (FACS) Calibur (BD Biosciences, Le Pont de Claix, France). Platelets were incubated with fluorescein isothiocyanate (FITC)-conjugated anti-human CD41 ($\alpha$IIb) and R-phycoerythrin (PE)-conjugated anti-human CD42b (GPIb$\alpha$) (both from Beckman Coulter, Villepinte, France) and FITC-conjugated anti-human activated $\alpha$IIbb3 (BDBiosciences) during 15 minutes at 22° C. Controls were performed using FITC mouse $IgG_1$ (Beckman Coulter), PE mouse $IgG_1$ (Beckman Coulter). Single color flow cytometric analysis of platelet receptors was performed using the GP screen assay (Biocytex, Marseille, France). The number of antigenic sites is determined by converting the fluorescence intensity into corresponding numbers of monoclonal antibodies bound per platelet based on a calibrated bead standard curve. Fibrinogen adhesion assay and epifluorescence characterization were performed as reported in as previously reported in the above-cited publication of Dunois-Lardé, except that activation was obtained in the presence of thrombin or of an agonist peptide of the PAR-1 thrombin receptor. Epifluorescence was analyzed at 494 nm and 522 nm (absorption and emission, respectively), using a high-resolution bioimaging platform (EMCCD MGi Plus Qimaging Rolera camera, Roper Scientific, Evry, France). Scanning electron microscopy was performed by adding platelets on glass slides coated with 2% BSA or fibrinogen (0.2 mg/ml) during 30 min. Thereafter, a drop of a solution containing HEPES 50 mM NaCl, 135 mM $Ca^{2+}$, 2 mM PFA 2%, and glutaraldehyde 4% was added on the slides for platelet fixation, and then the slides were incubated overnight in a bath containing the same solution. The day after, samples were washed and dehydrated with ethanol at 25%, 50%, 75%, 95% and finally at 100% then dried by air vacuum. Aggregation was performed using a dual-channel Whole Blood/Optical Lumi-Aggregometer (Model 700 Chrono log Corporation).

Megakaryocyte Mixing

The herringbone grooves create chaotic microvortices in the (Oyz) plane of the channel leading to lateral displacement of the cells (FIG. 16). They also enable the cells to break their trajectories to enter a trail rotated by 45° C. to the flow trajectories before exiting the trail and continuing in the main channel. Those chaotic displacements lead to a homogeneous lateral cell flow rate as described in FIG. 16b.

Megakaryocyte Capture

We define captured megakaryocytes by surface adherent megakaryocytes, independently of their translocation velocity (including non moving cells). We evaluated the megakaryocyte capture according to the different geometries of beams or posts (defined in FIG. 3 and FIG. 4). Results are shown in FIG. 7. Along the first part of the channel which is non textured, density of adherent megakaryocytes was very low ($\sigma<100$ $mm^{-2}$). In contrast, the density was much higher ($\sigma>750$ $mm^{-2}$), along the textured part of the channel. As control, smooth channels exhibited an undetectable surface density of megakaryocytes. Capture enhancement has also been verified for the inter post distances p=60 μm, p=85 μm and p=120 μm.

Along the last part that follows the textured portion and is empty of obstacles, we observe a sharp density difference between the textured channel ($\sigma\sim250$ $mm^2$) and the non-textured channel ($\sigma<10$ $mm^{-2}$). This is a direct consequence of the capture occurring in part 2 coupled with the translocation speeds of megakaryocytes (the distribution of translocation speed spreads from 0 $\mu m \cdot s^{-1}$ to 200 $\mu m \cdot s^{-1}$).

Effect of the Protein Surface Coating

On the vascular endothelial cells, VWF allows translocation of circulating platelets when subjected to high shear rates (>1000 $s^{-1}$) through binding of their GPIb receptors (Huizinga et al, Structures of Glycoprotein Ib$\alpha$ and Its complex with von Willebrand Factor A1 Domain", Science, vol. 297, no 5584, p. 1176-1179, 2002). In vitro, the adsorption of VWF allows megakaryocytes, platelets and proplatelets to translocate on the PDMS and glass surface (Dunois-Lardé et al, "Exposure of human megakaryocytes to high shear rates accelerates platelet production", Blood, vol. 114, no 9, p. 1875-1883, 2009). We compared the effect of VWF and BSA coating on the adhesion of megakaryocytes on the channel walls.

We performed four experiments with the channel geometry 2, coated with VWF and four experiments with channel geometry 2, coated with BSA. We compared the surface density of megakaryocytes at t=50 min.

Results are shown in FIG. 8. When coated with VWF, the mean megakaryocyte density is 54 $mm^{-2}$ in the smooth part of the channel and 275 $mm^{-2}$ in the textured part of the channel. When coated with BSA, the mean megakaryocyte density is 4 $mm^{-2}$ in the smooth part of the channel and 39 $mm^{-2}$ in the textured part of the channel. It verifies that the capture effect described in the previous paragraph occurs for both coatings. In addition, VWF sharply increases the density of adherent cells in the channel.

A third set of experiments has been done with fibrinogen coating. Although fibrinogen is known to bind megakaryocytes at a low shear rate, it was not possible to observe megakaryocyte capture at the high shear rates that were used to promote megakaryocyte elongation.

Those results do not describe the behavior of the cells on the surface in detail. We qualitatively observe an important decrease of a with distance along the x axis within the non-textured channel. In the textured channel, we observe a slight increase followed by a decrease of a along the textured length. These results are transient and result from the different transport mechanisms of the megakaryocytes.

Megakaryocyte and Platelet Transport

A cell owns two different transport modes: advection, yielding a speed of several $mm \cdot s^{-1}$, and translocation, yielding a speed of several $\mu m \cdot s^{-1}$. FIG. 10 presents different possible interactions between cells and walls. Using a post array, the cell can be captured by the channel walls as described by Dunois-Lardé et al (ibid.), but also by translocating on the top of the post or on the vertical sides of the post. When captured by a post, cells either follow their translocation on the channel wall, or are released in advection (FIG. 10.b), or else stop translocating (FIG. 10.c) and stay trapped behind a post. Those single cell events unravel the behavior on a larger scale described in the two former paragraphs.

Megakaryocyte Ruptures and Platelet Release

We observed platelet shedding from surface adherent megakaryocytes. When megakaryocytes are translocating on the channel walls, they establish transient interactions with VWF on the wall surface, which progressively lead to morphologic changes until platelet shedding from megakaryocytes. Shedding occurs when both elongation and cell body are translocating. This process is described in the above-cited publication of Dunois-Lardé and in the international patent application WO 2010/06382311. After a rupture, both entities continue translocating on the wall surface.

Shedding also occurs when the cell body translocates until being trapped around or behind a post (FIG. 10.c). On the time scale of several minutes, the megakaryocyte undergoes morphological changes leading to the formation of an elongation, that adopted a beads-on-a-thread structure, as previously reported in the above-cited publication of Dunois-Lardé. In addition, instead of full cell contacts with the coated surface, some elongations appeared to be freely moving (dangling) together with the flow, although the cells remained in the same position by at least one point of contact. As the size of the bead-on-a-thread elongation grows, some ruptures occur, releasing platelets and/or pro-platelets. FIG. 11 reports three different ruptures of the megakaryocyte elongation among ten (data not shown). The dangling release is detailed on a short time-scale in FIG. 12. After the rupture, the speed of the released proplatelet is measured to be 4 cm per second, which corresponds to the speed of the flow. We assume the released elements to be advected after the rupture.

The amount of platelets that can be released by each megakaryocyte can be estimated by long-time imaging of a single cell. Our observations showed that a megakaryocyte trapped on a post and subjected to shear can release 11 fragments/hour. These fragments have the shape of beads on a thread. We measured the size distribution of the released beads, fitting each of them as an ellipse on the frames of the video. Assuming revolution symmetry, we estimated the total volume of released beads and divided it by the volume of the smallest observed bead that we assume to be a platelet. With this method, we find a platelet yield of up to 350 platelets per megakaryocyte. In comparison, a human megakaryocyte is expected to convert in vivo into $10^2$-$10^3$ platelets (Thon et al, "Cytoskeletal mechanics of proplatelet maturation and platelet release", *J Cell Biol*, vol. 191, no 4, p. 961-874, 2010, and Thon et al., "Platelet Formation", *Seminars in Hematology*, vol. 47, no 3, p. 220-226, 2010).

Parallelization of Platelet Production from Megakaryocytes

We amplified the process of platelet production by fabricating parallelized channels patterned with arrays of pillars. All the following experiments used the geometry 3 described above. Geometry 3 owns a total of 168 770 pillars. FIGS. 13.a and 13.b is a detail of the pillar array showing a total of 66 pillars, where 48 pillars are involved in the megakaryocyte trapping or elongation process. Individually, we observe that a single pillar is able to trap several megakaryocytes. This process is transient and distance-dependent in the direction of the flow. FIG. 13.a depicts capture and elongation of cord blood megakaryocytes and FIG. 13.b depicts those of peripheral blood megakaryocytes.

In a "microfluidic device" configuration, a 20 mL agitated megakaryocyte suspension (200 000 megakaryocytes/mL) was circulating in closed-loop through 5 parallel devices fabricated following geometry 3 for 2 hours. In a "control" configuration, a 20 mL agitated megakaryocyte suspension was circulating in closed-loop without any microfluidic device in a single tubing (Tygon, 0.57 mm I.D., Saint-Gobain, France). To quantify platelet production, cell suspensions collected at the beginning and after 120 min perfusion either through the microfluidic device, or through the control system, were counted in a hemocytometer. Birefringent cells with a diameter between 1 µm and 4 µm were considered as platelets. FIGS. 13.c and 13.d show the results of the hemocytometer counting of platelet production from cord blood megakaryocytes and from peripheral blood megakaryocytes, respectively. FIG. 13.c shows at t=0 min, the platelet concentrations recovered in the microfluidic device and the control showed no significant difference (273 800 and 301 000 platelets/mL). At t=120 min, the concentrations were respectively 486 000±69 400 platelets/mL and 1 360 000±159 000 platelets/mL showing a significant difference (Student t test, paired samples, p<0.005). We assumed that this concentration increase is the consequence of the passage through the microfluidic device. FIG. 13.d indicates similar trends but no statistical analysis was performed between the platelet concentrations recovered in the microfluidic device and in the control.

Characterization of Platelet Produced in the Fluidic Device

After two hours of perfusion, the cell suspension circulating in the device contained larger amounts of platelets than that circulating in the control system. These platelets can then be sorted by the different methods described above. Platelets produced in the fluidic device displayed several characteristics that were comparable to those of natural platelets, i.e. platelets isolated from blood or circulating blood platelets. We found that these features are missing from the samples obtained from the control system consisting of all elements except for the fluidic channel. As shown on FIG. 14.a, expression of CD42b receptor was significantly higher in platelets produced by the fluidic device than in the platelet-like particles recovered in control samples (p<0.05). As observed using blood platelets, a clear population of $CD41^+CD42b^+$ elements was identified in the platelets produced by the microfluidic device, that was not found in the platelet-like particles recovered in control samples (FIG. 14.b). Interestingly, upon TRAP stimulation, platelets were able to undergo activation features similar to those known to characterize blood platelets, such as to increase their levels of binding of the PAC1 monoclonal antibody specific of the activated conformation of the αIIbβ3 receptor, a finding that was absent from the platelet-like particles recovered in control samples (FIGS. 14.c and 14.d). FIG. 15.a shows that the tubulin ring characteristic of platelets is present in the samples collected from the fluidic device but not from the control samples. Upon their activation by thrombin, platelets produced by the fluidic device displayed filopods, lamellipods and actin stress fibers, indicating that actin filaments are reorganized as in thrombin-activated platelets isolated from blood. Both hallmarks of platelet functions were missing from the control samples. Scanning electron microscopy (FIG. 15.b) shows the presence of filopodia and lamellipodia in TRAP activated platelets produced by the fluidic device, whereas these formations were not detected in the control samples. FIG. 15.c shows a platelet aggregate in the sample recovered from passage through the fluidic device. Again no such large aggregate was seen in platelets recovered in the control. Thus this report indicates for the first time that distinct features of platelets are observed in samples collected from exposure of megakaryocytes through a parallelized microfluidic device, that are missing from platelet-like particles recovered in control devoid of microfluidic chips.

The invention claimed is:

1. A fluidic device (1) for producing platelets from a suspension of megakaryocytes (5), comprising:
    a) a production chamber (3) comprising
    b) at least one channel (8) delimited by non-porous walls,
    c) at least one inlet opening (9) at one end in which a suspension of cells comprising megakaryocytes can be introduced and
    d) at least one outlet opening (10) at the other end, in which platelets can be collected;
    wherein at least one portion (11) of the inner surface of the walls of said channel (8) is textured with a plurality of obstacles.

2. The fluidic device according to claim 1, wherein said textured portion (11) of the inner surface of the channel (8) is further coated with a ligand with binding affinity for megakaryocytes.

3. The fluidic device according to claim 1, wherein the density, size and shape of said obstacles are determined so as to enable the capture of megakaryocytes on said textured portion of the inner surface of the channel for platelet shedding.

4. The fluidic device according to claim 1, wherein the obstacles are posts (12) or beams (15).

5. The fluidic device of claim 1, wherein said channel (8) has a substantially square or rectangular section.

6. The fluidic device of claim 1, wherein the obstacles are posts (12) with a substantially circular cross-section of a radius r, and said posts are arranged on the inner surface (13) of at least one portion of said channel to form a regular pattern with a hexagonal periodic structure, wherein:
    (i) the radius r is between 50 nm and 15 mm;
    (ii) the closest distance p between two post centers is equal to 100 nm;
    (iii) the angle a, which is the smallest angle defined by the longitudinal direction of the channel (14) and one of the lattice vectors of the hexagonal Bravais lattice is between 0 and 90°; and
    (iv) optionally said posts have a height h<H, wherein H refers to the smallest distance measured between two opposite walls in a section of the channel.

7. The fluidic device according to claim 6, wherein said channel has a height H that is between 5 μm and 1 mm.

8. The fluidic device according to claim 1, wherein said production chamber (3) comprises at least one or a plurality of parallel channels with a textured portion on their inner surfaces.

9. An ex vivo method for producing platelets from megakaryocytes, said method comprising:
    a) introducing a suspension of megakaryocytes into a fluidic device according to claim 1;
    b) subjecting said suspension to a flow under a shear rate suitable for elongation, fragmentation of the megakaryocytes and platelet release in the channel of the production chamber; and
    c) collecting platelets at the outlet of the channel.

10. The method according to claim 9, wherein the flow rate is fixed within a range that subjects said megakaryocytes in the textured portion of the channel to a maximum wall shear rate $\gamma_{max}$ not exceeding 30000 s$^{-1}$.

11. The method according to claim 9, wherein the collected platelets at the outlet of the channel further contain naked nuclei and/or intact megakaryocytes, said method further comprising the step of purifying, enriching or separating the platelets from said suspension.

12. The method according to claim 9, wherein said suspension is a suspension obtained by the following steps: (i) providing megakaryocyte progenitor and/or stem cells, (ii) expanding said megakaryocyte progenitor and/or stem cells, and, (iii) differentiating the expanded cells into megakaryocytes.

13. The method of claim 12, wherein the megakaryocyte progenitor and/or stem cells are selected from the group consisting of hematopoietic stem cells, embryonic stem cells and induced pluripotent stem cells.

14. The method according to claim 9, wherein said suspension of megakaryocytes is homogenized and/or purified prior to entering in the production chamber.

15. The method according to claim 9, wherein said platelets are sorted at the outlet of the channel by a method selected from the group consisting of cross flow filtration, laminar flow, dielectrophoresis, optical force, magnetic force, acoustic force, or inertial forces.

16. The method according to claim 9, wherein said platelets are functional platelets which can be activated like circulating blood platelets.

17. The fluidic device according to claim 2, wherein said ligand with binding affinity for megakaryocytes is selected from von Willebrand factor (VWF), or a biologically functional fragment thereof, or fibrinogen or fibronectin.

18. The method according to claim 10, wherein said maximum wall shear rate does not exceed 10000 s$^{-1}$.

19. The method according to claim 10, wherein said maximum wall shear rate does not exceed 8000 s$^{-1}$.

20. The method according to claim 10, wherein said maximum wall shear rate does not exceed 5000 s$^{-1}$.

21. The fluidic device according to claim 6, wherein the radius r is between 500 nm and 1.5 mm.

22. The fluidic device according to claim 6, wherein the closest distance p between two post centers is between 100 nm and 50 mm.

23. The fluidic device according to claim 6, wherein the closest distance p between two post centers is between 500 nm and 10 mm.

24. The fluidic device according to claim 6, wherein the closest distance p between two post centers is between 5 μm and 1 mm.

25. The fluidic device according to claim 6, wherein one of the lattice vectors of the hexagonal Bravais lattice is between 0 and 30°.

26. The fluidic device according to claim 8, wherein said production chamber comprises between 2 and 106 channels.

27. The method according to claim 18, wherein said maximum wall shear rate does not exceed 5000 s$^{-1}$.

* * * * *